United States Patent
Chok et al.

(10) Patent No.: US 9,921,204 B2
(45) Date of Patent: Mar. 20, 2018

(54) SYSTEM AND METHOD FOR FLUID COMPOSITION CHARACTERIZATION

(71) Applicant: Weatherford Technology Holdings, LLC, Houston, TX (US)

(72) Inventors: Hamed Chok, Houston, TX (US); Endre Anderssen, Houston, TX (US); Jess V. Ford, Weatherford, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 191 days.

(21) Appl. No.: 14/931,729

(22) Filed: Nov. 3, 2015

(65) Prior Publication Data

US 2017/0122923 A1    May 4, 2017

(51) Int. Cl.
| | |
|---|---|
| G01N 21/25 | (2006.01) |
| G01N 33/28 | (2006.01) |
| G01N 21/31 | (2006.01) |
| G01J 3/28 | (2006.01) |
| G01N 21/3577 | (2014.01) |
| E21B 49/08 | (2006.01) |
| G01N 21/85 | (2006.01) |

(52) U.S. Cl.
CPC ............ *G01N 33/2823* (2013.01); *G01J 3/28* (2013.01); *G01N 21/25* (2013.01); *G01N 21/31* (2013.01); *G01N 21/3577* (2013.01); *E21B 49/088* (2013.01); *G01J 2003/2836* (2013.01); *G01N 21/85* (2013.01); *G01N 2021/3129* (2013.01)

(58) Field of Classification Search
CPC ........ G01N 21/28; G01N 21/27; G01N 21/25; G01N 21/03; G01N 33/28
See application file for complete search history.

(56) References Cited

U.S. PATENT DOCUMENTS

| | | | |
|---|---|---|---|
| 8,164,050 B2 | 4/2012 | Ford et al. | |
| 8,411,262 B2 | 4/2013 | Ford et al. | |
| 8,536,516 B2 | 9/2013 | Ford et al. | |
| 8,735,803 B2 | 5/2014 | Ford et al. | |
| 2014/0360257 A1* | 12/2014 | Indo ................... | E21B 47/102 73/152.28 |
| 2015/0204189 A1 | 7/2015 | Indo et al. | |

FOREIGN PATENT DOCUMENTS

WO    2015/014694 A1    2/2015

OTHER PUBLICATIONS

Int'l Search Report and Written Opinion in counterpart PCT Appl. PCT/US2016/054664, dated Dec. 21, 2016, 11-pgs.

* cited by examiner

*Primary Examiner* — Abdullahi Nur
(74) *Attorney, Agent, or Firm* — Blank Rome LLP

(57) ABSTRACT

Systems and methods for predicting fluid composition in a reservoir formation are disclosed. To accurately and efficiently predict the composition of a sample fluid, an absorption spectrum is obtained over a prefixed set of wavelength channels and a set of basis spectra is received for all constituents of interest in the sample fluid. A set of a-priori constraints on the obtained absorption spectrum and constituent properties to be determined is then obtained, before calculating a joint probability distribution of all constituents of interest based on the obtained spectrum, basis spectra and a-priori constraints. In one embodiment, qualitative states are also computed for all constituents of interest based on the obtained spectrum, basis spectra and a-priori constraints.

26 Claims, 13 Drawing Sheets

SYSTEM AND METHOD FOR FLUID COMPOSITION CHARACTERIZATION

TECHNICAL FIELD

This disclosure relates generally to the field of characterization of fluid compositions in wellbores and in particular to methods and systems for spectroscopy-based fluid composition characterization.

BACKGROUND

Formation fluid obtained from a reservoir generally contains a number of natural constituents, such as water, super critical gas, and liquid hydrocarbons. In addition to these natural constituents, the composition of the formation fluid may also include contaminants such as filtrate including water-based mud or oil-based mud, used during drilling operations.

Constituents of this formation fluid may be identified by sampling the fluid and then conducting an analysis on the composition of the sampled fluid. The analysis is generally performed by making special measurements of the fluid to characterize the composition and as such infer many properties of interest about the fluid. Knowledge of these properties is useful in characterizing the reservoir and in making many engineering and business decisions.

One type of special measurement that can be made on sampled fluid is density measurements. For example, density measurements are sometimes made at fixed time intervals, and analyzed to estimate the sample's quality. The repeated density measurements can be used to plot the change in density over time. Characteristics of this density-time plot can then be used to assess the composition and contamination level of the sampled fluid. Other types of measurements that can be used in characterizing fluid composition include monitoring density, pressure, temperature and the like.

In addition to making these measurements, various other tools can be used to perform analysis of downhole fluids. For example, spectrophotometers, spectrometers, spectrofluorometers, refractive index analyzers, and similar devices can be used to analyze downhole fluids by utilizing appropriate sensors to measure the fluid's spectral response. Although useful and effective, these types of measurements and tools can be complex to perform and hard to operate in the downhole environment. Moreover, the results of the measurements may not provide the level of detailed information needed to accurately characterize the reservoir.

Though various techniques have been used in the past for characterizing fluid composition of a fluid sample, most of these techniques lack the level of accuracy desired and may also be inefficient. The following disclosure addresses these and other issues.

SUMMARY

In one embodiment of obtaining composition of a sample fluid from a source, an absorption spectrum of the sample fluid is obtained over a set of one or more wavelength channels, and a set of basis spectra is received for one or more constituents of the sample fluid. One or more constraints are calculated based on the absorption spectrum and one or more properties of the one or more constituents. A solution space is characterized for the composition of the sample fluid in terms of the one or more constituents based on the absorption spectrum, the basis spectra, and the one or more constraints; and the solution space for the composition is associated with the source of the sample fluid.

The absorption spectrum of the sample fluid can be obtained utilizing an optical sensor tool, and the set of the basis spectra for the one or more constituents of the sample fluid can be obtained from a stored collection of base constituent spectra at a plurality of temperatures and pressures. The solution space for the composition can be associated with the source of the sample fluid by associating the solution space with a portion of a downhole formation traversed by a borehole.

The one or more constraints can include one or more of: a maximum tool measurement error on any one of the one or more wavelength channels; a maximum measurable absorption value on any one of the one or more wavelength channels; maximum and minimum mixture coefficient thresholds for at least one of the one or more constituents; a set of linear constraints that can be used to approximate a general form of a cumulative spectrum of an Urbach tail and baseline offset; a required sum of the mixture coefficients of the one or more constituents; a required mixture of the basis spectra, the Urbach tail, and the baseline offset relative to obtained spectrum of a fluid sample; and upper and lower bounds on a level of error in obtained absorption in each spectrum in the set of basis spectra over each of the one or more wavelength channels.

In the method, a density value can be obtained for each one of the one or more constituents and the sample fluid, and a joint prior density function can be obtained for the mixture coefficients of the one or more constituents.

To characterize the solution space for the composition of the sample, a linear inequality system can be calculated where the linear inequality system defines a complete polyhedral solution set. One or more parameter thresholds can be adjusted to ensure a non-empty solution set for the complete polyhedral solution set. The complete polyhedral solution set can be approximated by embedding the complete polyhedral solution set into a polyhedral solution set of lesser complexity. A vertex set can be enumerated of the complete or embedded polyhedral solution set. A simplicial decomposition can be performed on the enumerated vertex set to create one or more simplices, and a volume of each of the one or more simplices can be calculated. A Dirichlet distribution can be calculated over each of the one or more simplexes, and a beta distribution can be calculated over each of the one or more simplexes for each of the one or more constituents from the Dirichlet distribution.

To calculate the volume of each of the one or more simplices, the joint prior density function can be integrated over each of the one or more simplices. To characterize the solution space for the composition of the sample fluid, a weight value can be calculated for each enumerated vertex in the enumerated vertex set based on a joint prior density function for the mixture coefficients of the one or more constituents and a performed simplicial decomposition.

The weight value for each enumerated vertex in the vertex set can be calculated based on a set of distribution moments over each of the one or more simplices in the simplicial decomposition. The set of distribution moments can be calculated by performing integration of appropriate integrands over each of the one or more simplices in the simplicial decomposition and based on the joint prior density function. Calculate the vertex weight values for each enumerated vertex in the vertex set can be obtained as a result of an optimization method for casting the distribution over each of the one or more simplices in the simplicial decomposition from the calculated distribution moments.

To characterize the solution space for the composition of the sample fluid, the volume of each of the one or more simplices can be calculated based on a joint prior density function, and a mixture Dirichlet distribution can be calculated over the complete polyhedral set. The mixture beta distribution can be calculated from the mixture Dirichlet distribution over the complete polyhedral set for each of the one or more constituents, and the mixture Dirichlet distribution can be calculated by linearly combining individual Dirichlet distributions. To linearly combine individual Dirichlet distributions, weighting values can be calculated based on respective simplex volumes relative to a total polyhedral volume.

According to the method, a minimum confidence threshold and a minimum presence threshold can be obtained for each of the one or more constituents. Also, using the mixture Dirichlet distribution, a qualitative state can be calculated for each of the one or more constituents based on obtained minimum confidence and minimum presence thresholds.

In another embodiment of characterizing composition of a sample fluid, an absorption spectrum is obtained of the sample fluid over a set of one or more wavelength channels. A set of basis spectra is received for one or more constituents of the sample fluid, and one or more constraints are calculated based on the absorption spectrum and one or more properties of the one or more constituents. One or more qualitative states are calculated for the one or more constituents based on the absorption spectrum, basis spectra, and the one or more constraints.

At least one of the one or more constraints can include one or more of: a maximum tool measurement error on any one of the one or more wavelength channels; a maximum measurable absorption value on any one of the one or more wavelength channels; maximum and minimum mixture coefficient thresholds for at least one of the one or more constituents; a set of linear constraints that can be used to approximate a general form of a cumulative spectrum of an Urbach tail and baseline offset; required sum of mixture coefficients of the one or more constituents; required mixture of basis spectra, Urbach tail, and baseline offset relative to obtained spectrum of a fluid sample; upper and lower bounds on a level of error in obtained absorption in each spectrum in the set of basis spectra over each of the one or more wavelength channels; a minimum presence threshold; and a minimum confidence threshold.

In the method, a density value can be obtained for each one of the one or more constituents and the fluid sample; and incorporating the density values in the one or more constraints. To calculate the one or more qualitative states, a linear inequality system is calculated, where the linear inequality system defines a complete polyhedral solution set. One or more parameter thresholds are adjusted to ensure a non-empty solution set for the complete polyhedral solution set. The complete polyhedral solution set is approximated by embedding the complete polyhedral solution set into a polyhedral solution set of lesser complexity. The method enumerates a vertex set of the complete or embedding polyhedral solution set.

A simplicial decomposition is performed on the enumerated vertex set to create one or more simplices. A volume is calculated for each of the one or more simplices, and at least one of the one or more simplices is divided into a frustum and a remaining portion by a hyperplane defined by a minimum presence threshold. A volume of the each of the generated one or more frusta is calculated, and the one or more qualitative states for the one or more constituents are calculated by calculating state probabilities for each of the one or more constituents based on the minimum confidence threshold, the one or more simplex volumes, and the one or more frustum volumes.

In an embodiment of the present disclosure, a non-transitory program storage device, readable by a processor and comprising instructions stored thereon to cause one or more processors, can characterize composition of a sample fluid according to the above techniques. Additionally, a system having a memory, a communication interface, and a processor operatively coupled to the memory and the communication interface can characterize composition of a sample fluid according to the above techniques.

The foregoing summary is not intended to summarize each potential embodiment or every aspect of the present disclosure.

DESCRIPTION OF DISCLOSED EMBODIMENTS

Correct qualitative and quantitative identification of the constituents of interest in a sampled fluid is important in characterizing a reservoir and thus helpful in the making of many engineering and business decisions.

Figure 1:
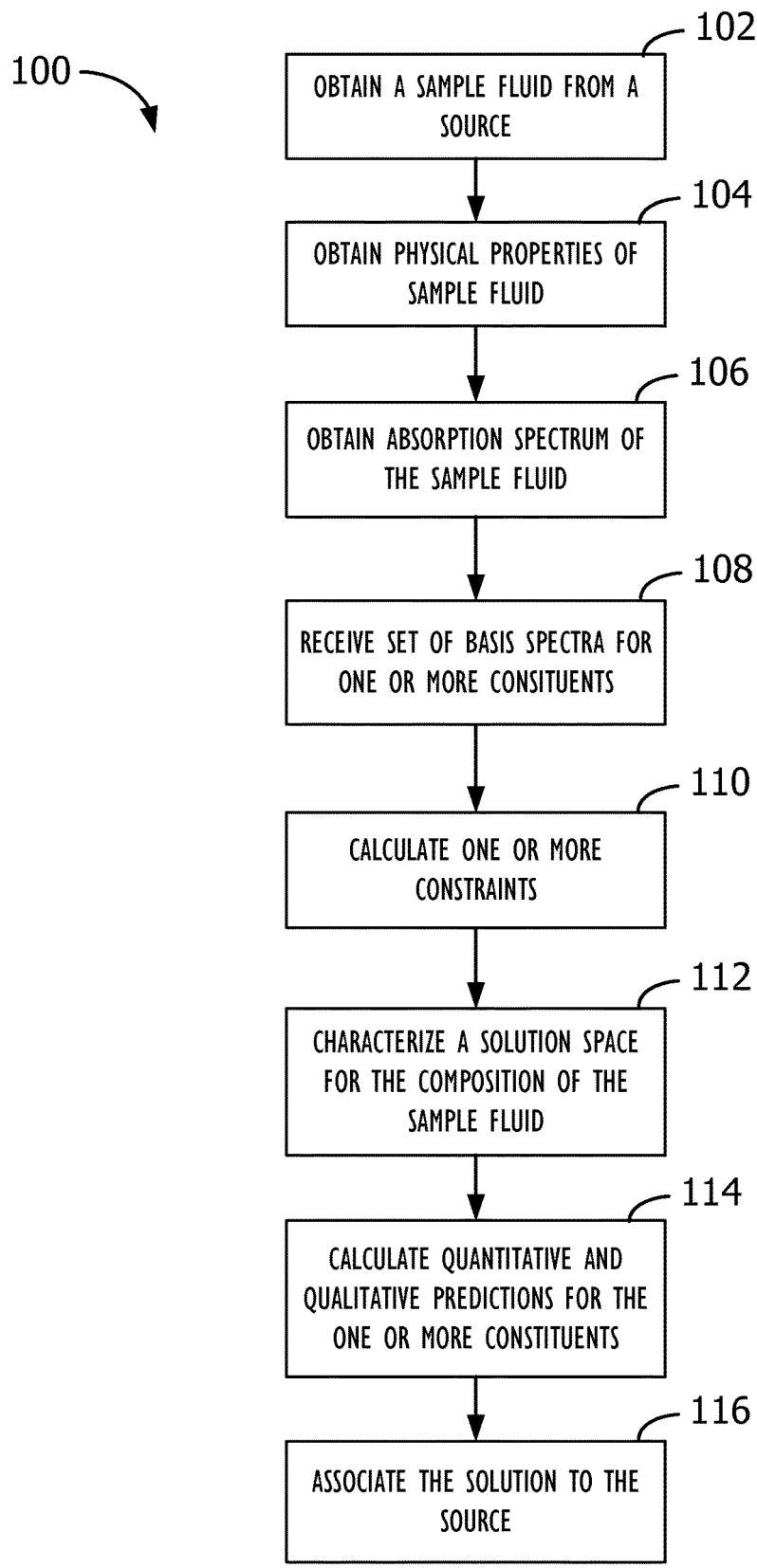
FIG. 1 shows a flowchart for characterizing composition of a sample fluid according to the present disclosure.

FIG. 1 shows a flowchart of a process 100 for characterizing composition of a sample fluid according to the present disclosure. In the process 100, a sample fluid is obtained (Block 102), physical properties of the sample fluid are obtained (Block 104), and an absorption spectrum is obtained of the sample fluid over a set of one or more wavelength channels (Block 106). This can be done in a number of ways. The physical fluid properties can be measured and can include density, viscosity, dielectric, and the like, which may be utilized in the calculation process.

In one embodiment, for example, the process 100 of characterizing the sample fluid begins by utilizing an optical sensor tool to generate the absorption spectrum of the sample fluid at a finite set of fixed wavelength channels. Then, as discussed below, the recorded absorption spectrum is then used to characterize both qualitatively and quantitatively the composition of the sample fluid in terms of the constituents of interest. In one embodiment, a qualitative estimate classifies a constituent of interest with respect to the sample fluid as being in one of three states: present, absent, or indeterminate. A quantitative estimate, on the other hand, may provide a single value or a range of values for the concentration of any constituent of interest.

Continuing with the process 100 once the absorption spectrum is obtained, a set of basis spectra is received for one or more constituents of the sample fluid (Block 106). In order to calculate the composition of any sample fluid from its observed spectrum at known temperature and pressure conditions, the existence of the spectra of the underlying base constituents at the same or near-same temperature and pressure conditions is presumed. The collection of base constituent spectra at one given temperature and pressure is referred to as a basis spectra. In one embodiment, a basis spectra is assumed to include a methane spectrum, a carbon dioxide spectrum, a water spectrum, a C2-C5 spectrum, a C6+ spectrum, and an aromatic spectrum. Each of the C2-C5, C6+, and the aromatic spectra may represent an aggregate of several other lower level constituent spectra.

In addition to the above basis spectra, in one embodiment, it may be assumed that the additional constituent of asphaltene manifests itself spectrally in the form of an Urbach tail, which is a form of an exponential spectral decay in terms of the wavelength. The form of the Urbach tail is known in the art and is a function of the asphaltene concentration in the sample fluid.

Thus, an assumption may be made that any measured spectrum for a sample fluid is comprised of a mixture of any of the above basis spectra, asphaltene, a baseline offset, and an unassigned residual spectrum of a predefined maximum potential concentration. It may also be assumed that the optical sensor tool used to measure the absorption levels has an intrinsic measurement error that can be bounded.

In the process 100, one or more constraints are then calculated based on the absorption spectrum obtained in Block 106 and one or more properties of the one or more constituents in addition to any other physical properties obtained in Block 104 (Block 110). Given the observed spectrum for the sample fluid and additional measured physical properties, in one embodiment for example, a linear constraint-based formulation can be developed for characterizing all the constituents in the fluid mixture from its spectrum and measured properties by virtue of the following assertions:

Fluid mixtures of elemental constituents obey Beer's law. Therefore their respective spectra admit an additive properly;

Error terms in the observed spectrum yielded by the combined tool measurement noise and spectral errors in the collections of the basis spectra can be bounded a priori or constrained from an optimization procedure;

The combined spectral response of asphaltene and the presence of optical scattering is formalized via the Urbach tail form plus an offset term which can be approximated by means of linear constraints;

A possible uncharacterized residual spectrum in the fluid mixture can also be expressed by means of linear constraints; and Additional physical properties such as fluid density and viscosity can be expressed linearly in terms of the fluid composition.

When stated in terms of a linear formulation, characterizing the fluid composition can be translated into a problem of combinatorial computational geometry. To simplify this problem, in one embodiment, it may be assumed that the spectral error term is uniformly distributed. In such an embodiment, the computational geometric framework for characterizing the fluid composition can be further utilized to allow for a more general statistical formulation by relaxing the uniformity assumption on the error term.

Ultimately, the process 100 involves characterizing a solution space (Block 112) for the composition of the sample fluid in terms of the one or more constituents based on the absorption spectrum (Block 106), the fluid physical properties (Block 104), the basis spectra (Block 108), and the one or more constraints (Block 110). Using said characterization, the process 100 calculates one or more quantitative and qualitative predictions for the one or more constituents (Block 114).

In particular, the collection of the linear constraints discussed above effectively defines the solution set encompassing all possible compositions of the fluid mixture whose spectrum is recorded. Because these constraints represent a fluid mixture, any solution satisfying such constraints may be identified by the associated mixture coefficients, which may be expressed in mass fractions. Furthermore, knowing the density of each of the individual mixture constituents, the constraints and thus any underlying solution may be equivalently expressed via the concentration of each the mixture constituents.

In the end, the process associates the solution space for the composition of the sample fluid with the source (Block 116), which can be a particular permeable zone, depth, or the like of a formation downhole traversed by a borehole. Knowledge of the composition of the formation fluid downhole can then drive a number of useful activities in the exploration, completion, and production of formation fluids from a reservoir. For example, knowing the composition of fluid in different portions of a formation downhole allow drilling operators to direct drilling operations, allow a service company to define a suitable completion system to produce the fluid, and provides a whole host of concrete and useful benefits recognized by one skilled in the art.

Having an overall understanding of the process 100 for characterizing composition of a sample fluid according to the present disclosure, discussion now turns to the characterization techniques in more detail.

Figure 2A:
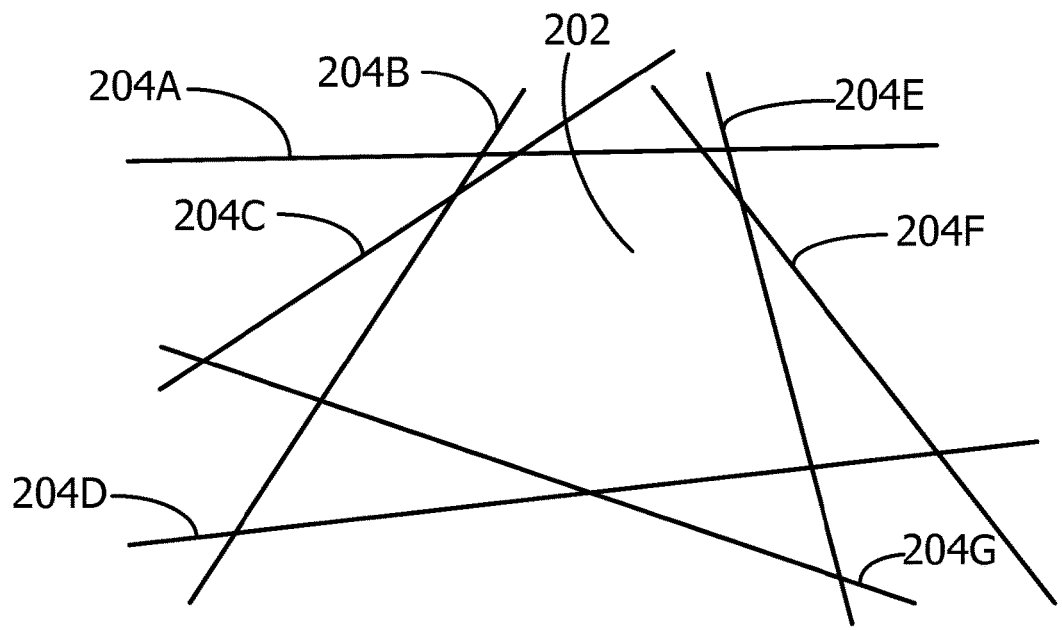
FIG. 2A shows multiple hyperplanes each representing a constraint for a fluid composition, according to one or more disclosed embodiments.

As the constraints are all linear, it follows that geometrically the underlying solution set corresponds to the space within a bounded multidimensional polyhedron (i.e., polytope) having dimensions on the order of the number of constituents. An example of such a polytope is illustrated in FIG. 2A, where the space 202 defining the polytope represents the solution set. As can be seen the space 202 is bounded by hyperplanes 204A-204G which are defined by the linear constraints.

Figure 2B:
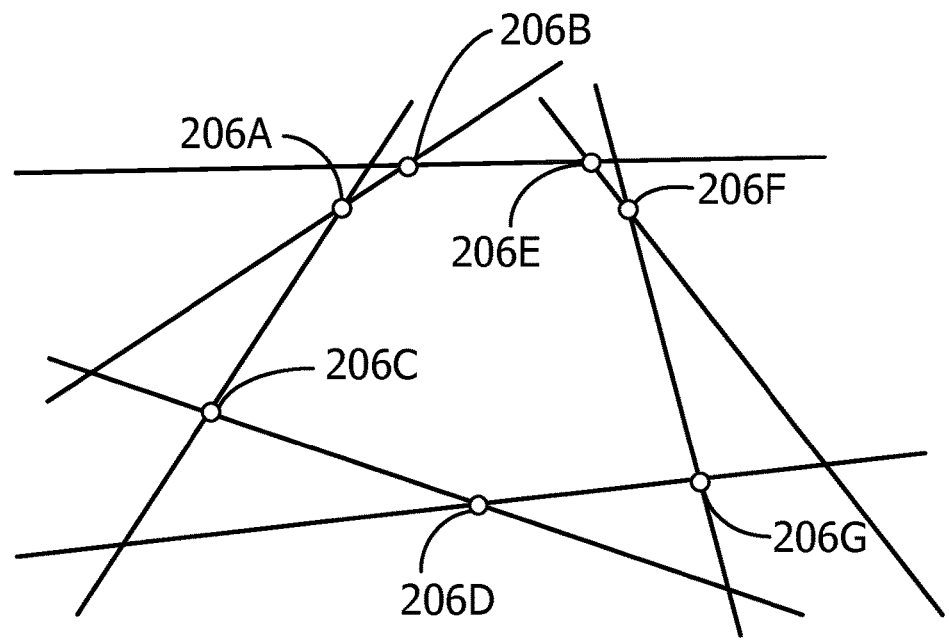
FIG. 2B shows the multiple hyperplanes of FIG. 2A along with a vertex set that defines a solution set, according to one or more disclosed embodiments.
Figure 3:
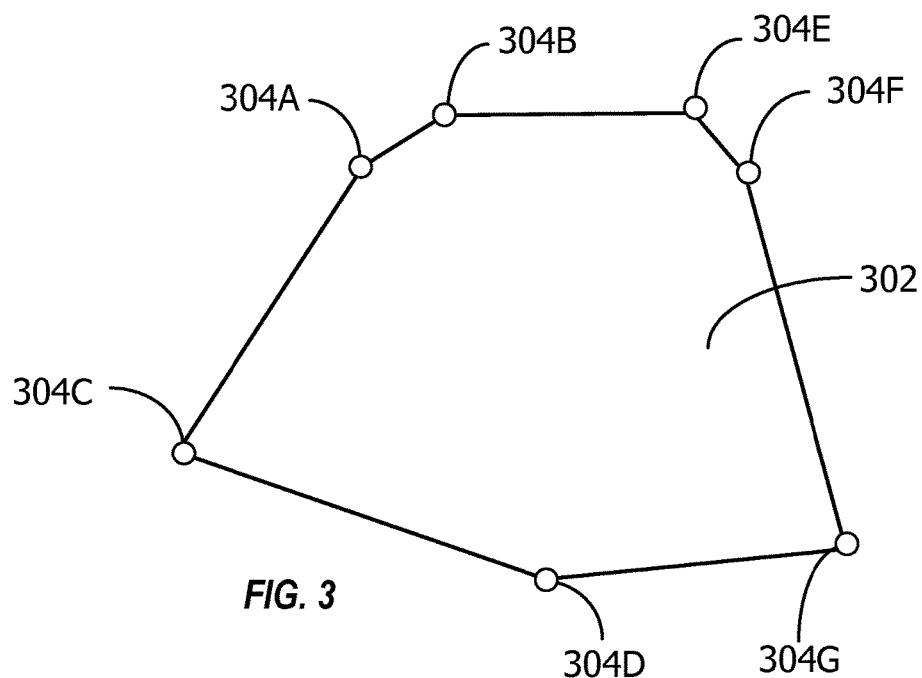
FIG. 3 shows a convex hull defining the solution set which was represented by the vertex set of FIG. 2B, according to one or more disclosed embodiments.

In this manner, characterizing the fluid composition mixture coefficients (or alternatively, concentrations) translates to characterizing the associated polytope. Such a polytope can be sufficiently expressed via a set of vertices that lie on the boundaries of the polytope and whose convex hull encloses the entire polytope. This is illustrated in FIG. 2B. As shown, the vertices 206A-206G are corners where (in the case of this two dimensional example) two lines meet. More generally, each of these vertices lies in the intersection of multiple hyperplanes on the order of the dimension of these vertices. In one embodiment, these corners represent extreme compositions. The convex hull of the vertex set 206A-206G determines the complete solution set. The convex hull and the polytope vertices of FIG. 2B are illustrated in FIG. 3. As is known in the art, the convex hull of the vertex set 302 is determined by all possible mixture combinations of the vertices 304A-304G where the mixture coefficients in any of the said combinations are all positive and summing to one.

In obtaining the solution set, one important algorithmic step may involve enumerating the polytope vertices 304A-304G, given the bounding hyperplanes 104A-104G (i.e., linear constraints). Enumerating polytope vertices exactly may, however, prove to be too prohibitive for real-time purposes when the problem size is large. The size of the problem, generally, depends on the number of constituents and the total number of linear constraints, which in turn depends on the number of wavelength channels. In one embodiment, to simplify the step of enumerating the polytope vertices, the original polytope is replaced by one of intrinsically lesser complexity which still satisfies well-chosen constraints. This is equivalent to embedding the original polytope into a larger but sufficiently tight polytope. This polytope embedding amounts to computing a well-chosen different set of bounding hyperplanes that affords vertex enumeration in real-time.

Figure 4:
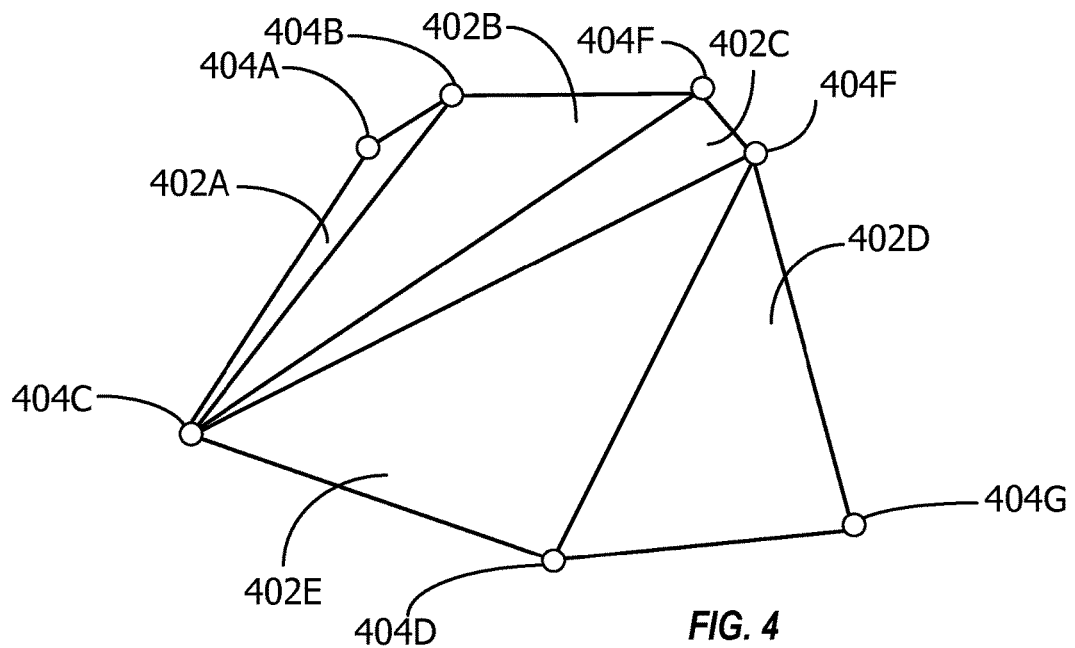
FIG. 4 shows a simplicial decomposition of the convex hull of FIG. 3, according to one or more disclosed embodiments.

As polytopes may be difficult to characterize directly, a more efficient characterization of the solution space (or approximation thereof) may be done by decomposing the underlying polytope into a more manageable geometric sets. In one embodiment, this is done by performing a simplicial decomposition of the underlying polytope. This involves dissecting the solution space into a set of high-order triangles (referred to herein as simplices) given the vertex set defining its convex hull. This is illustrated in FIG. 4, where the polytope's convex hull 302 of FIG. 3 is decomposed into 5 simplices 402A-402E. As shown, the simplices 402A-402E are defined by the vertices 404A-404G. In this manner, the distribution of the solution within the complete set may be expressed in terms of the individual distributions within each simplex in the decomposition. Assuming either a uniform or known (prior) arbitrary probability distribution over the complete solution set, as discussed in detail below, algorithms may be developed to estimate the fluid composition both qualitatively and quantitatively.

Qualitative composition estimation for any constituent of interest starts, in one embodiment, by discretizing the complete mixture coefficient range into two classes: present and absent. Class discretization depends on a threshold that separates out significant mixture values from insignificant ones. In one embodiment, this threshold is predetermined. In alternative embodiments, the threshold may be set by a user. This threshold can be used as an additional linear constraint defining the solution class partitioning over the complete solution set. When a uniform probability density function is assumed, dividing the volume of the portion of the polytope that is above the threshold constraint by the volume of the whole polytope results in the probability that a constituent of interest is present. The complete polytope volume can be easily computed because it can be directly obtained by summing the volumes of all simplices in the simplicial decomposition, and the volume of a simplex is computable knowing its vertex set using formulae known in the art.

For any simplex in the decomposition, the threshold constraint either cuts off the simplex into two parts or will lie entirely above or below the simplex. In general, the intersection of the space above the threshold constraint (i.e., the hyperplane representing the threshold constraint) and any simplex defines a frustum structure whose volume can be computed algorithmically from the simplex vertex set and the cutting hyperplane. Procedures for computing the volume of a frustum are well known in the art. The total volume of the space above the threshold constraint can thus be obtained by summing the volumes of all generated frusta (or complements thereof depending on the position of any underlying simplex relative to the cutting hyperplane).

In one embodiment, qualifying the presence of any constituent is based on the volume ratio obtained by dividing the total volume above the cutting hyperplane by the total volumes from all simplices where the threshold hyperplane is defined with respect to the associated constituent of interest. In one embodiment, when the presence probability of any constituent (i.e., aforementioned volume ratio) surpasses a minimum confidence threshold, then the constituent of interest is likely present in the mixture and is flagged as such. If such probability is less than one minus the minimum confidence threshold, then the constituent of interest is not likely to be present in the mixture and it is flagged accordingly. When, neither of these two evaluations involving the volume ratio holds true, it is uncertain whether or not the constituent of interest is present and it is therefore flagged as indeterminate. The minimum confidence threshold may be predetermined, set by a user or adaptable depending on other criteria.

Quantitative composition can be probabilistically characterized by a multidimensional joint probability density function defined over the solution-associated polytope. The probability distribution of the solution over any simplex in the decomposition can be represented by a Dirichlet density function. When a uniform prior probability function is assumed over the polyhedral solution set, the solution distribution over any simplex is the uniform Dirichlet distribution. The solution probability distribution over the entire polytope is the mixture probability distribution obtained from adding up all the individual Dirichlet distributions over all simplices weighted proportionally to each respective simplex volume. When the joint probability distribution is a mixture of Dirichlet distributions, then the probability distribution of any individual constituent is a mixture beta distribution. The individual probability distribution for any constituent can be used to define confidence intervals on the fraction of the underlying constituent. The following mathematical formulations provide more detail about the process used to obtain the solution set and its qualitative and quantitative characterizations.

A. Mixture Coefficients Limit Constraints

The set of all plausible l-composition vectors, where/is the number of constituents of interest, can be written as $\{(a_i)_{i=1\ldots l} | \forall i=1\ldots l, a_i \geq 0, \Sigma_{i=1\ldots l} a_i = 1\}$. Predefined limits on the mixture coefficient of each constituent may be established from prior domain knowledge, hence let $a_i^{min}$ and $a_i^{max}$ denote the minimum and maximum of the mixture coefficient for the $i^{th}$ constituent, respectively. This a priori set of l-composition vectors can be denoted as below:

$$\{(a_i)_{i=1\ldots l} | \forall i=1\ldots l, a_i \geq 0, \Sigma_{i=1}^l a_i = 1 a_i^{min} \leq a_i \leq a_i^{max}\} \quad (1)$$

B. Basis Spectra Fluid Mixture Constraints

Furthermore, given an observed spectrum m and a constituent set of spectra $\{s_i\}_{i=1\ldots l-1}$, both measured at an n-channel sequence $(\lambda_j)_{j=1\ldots n}$ and at fixed temperature and pressure, m may be expressed as follows:

$$m = \Sigma_{i=1}^{l-1} a_i s_i + u + (1 - \Sigma_{i=1}^l a_i) r + \in \quad (2)$$

Where u denotes the total spectrum resulting from any baseline offset plus any Urbach tail, r denotes an uncharacterized residual spectrum, and $\in$ denotes the noise spectrum.

It may be further required that the total composition of the residual spectrum does not surpass a threshold $\Delta$ i.e., $(1-\Sigma_{i=1}^l a_i) \leq \Delta$. Furthermore, since there is an intrinsic maximum absorbance value measured by the optical sensor tool, which may be denoted by $\theta_{max}$, we must have $0 \leq r_j \leq \theta_{max}$ $\forall j=1 \ldots n$, where $r=(r_j)_{j=1\ldots n}$. It follows that $$0 \leq (1-\Sigma_{i=1}^l a_i) r_j \leq \Delta \theta_{max} \forall j=1 \ldots n$$

and consequently that $$0 \leq m_j - (\Sigma_{i=1}^{l-1} a_i s_{i,j} + u_j + \in_j) \leq \Delta \theta_{max} \forall j=1 \ldots n.$$

In one embodiment, a further requirement may be made that the intrinsic tool noise be within $\pm \in_{max}$. Accordingly, the basis spectra mixture constraints imply that the composition vector a must be confined in the following set:

$$\{(a_i)_{i=1\ldots l} | \forall i=1\ldots l, \forall j=1\ldots n, a_i \geq 0, 1-\Delta \leq \Sigma_{i=1}^l,$$
$$a_i \leq 1, a_i^{min} \leq a_i \leq a_i^{max}, 0 \leq m_j - (\Sigma_{i=1}^{l-1} a_i s_{i,j} + u_j +$$
$$\in_j) \leq \Delta \theta_{max}, -\in_{max} \leq \in_j \leq \in_{max}\} \quad (3)$$

The set of plausible compositions can be further refined, in one embodiment, by incorporating the constraints relating to the baseline offset and Urbach tail. This can be done by requiring that the u spectrum satisfy $u_j = Ae^{E_0/\lambda_j} + b \forall j=1 \ldots n$ for some $A \in \mathbb{R}_+^*$, $b \in \mathbb{R}$, and $E_0 \in \mathbb{R}_+^*$. If $f(\lambda) = Ae^{E_0/\lambda} + b \forall \lambda \in \mathbb{R}_+^*$ then it can be verified that:

$$\text{sign}\left(\frac{df(\lambda)}{d\lambda}\right) = \text{sign}\left(-\frac{AE_0}{\lambda^2}e^{E_0/\lambda}\right) = -1 \forall A \in \mathbb{R}_+^*, E_0 \in \mathbb{R}_+^*, \quad (4)$$
$$\lambda \in \mathbb{R}_+^*$$

$$\text{sign}\left(\frac{d^2 f(\lambda)}{d\lambda^2}\right) = \text{sign}\left(A\left(\frac{E_0^2}{\lambda^4}e^{E_0/\lambda} + \frac{2E_0}{\lambda^3}e^{E_0/\lambda}\right)\right) = +1 \forall A \in \mathbb{R}_+^*, \quad (5)$$
$$E_0 \in \mathbb{R}_+^*, \lambda \in \mathbb{R}_+^*$$

$$\text{sign}\left(\frac{d^3 f(\lambda)}{d\lambda^3}\right) = \quad (6)$$
$$\text{sign}\left(-A\left(\frac{E_0^3}{\lambda^6}e^{E_0/\lambda} + \frac{6E_0^2}{\lambda^5}e^{E_0/\lambda} + \frac{6E_0}{\lambda^4}e^{E_0/\lambda}\right)\right) = -1 \forall A \in \mathbb{R}_+^*,$$
$$E_0 \in \mathbb{R}_+^*, \lambda \in \mathbb{R}_+^*$$

More generally, it can be verified that:

$$\text{sign}\left(\frac{d^k f(\lambda)}{d\lambda^k}\right) = (-1)^k \forall A \in \mathbb{R}_+^*, E_0 \in \mathbb{R}_+^*, \lambda \in \mathbb{R}_+^*, k \in N^* \quad (7)$$

To this end, the following set contains all functions satisfying (7) $\forall k \in [[1, k_{max}]]$:

$$\left\{f: \mathbb{R}_+^* \to \mathbb{R} \;\middle|\; \text{sign}\left(\frac{d^k f(\lambda)}{d\lambda^k}\right) = (-1)^k \forall A \in \mathbb{R}_+^*, \quad (8)\right.$$
$$\left. E_0 \in \mathbb{R}_+^*, \lambda \in \mathbb{R}_+^*, k \in [[1, k_{max}]]\right\}$$

For a sufficiently large $k_{max}$, the above set of functions (8) may be used as a very good approximate characterization of the function family $f(\lambda) = Ae^{E_0/\lambda} + b$ for all positive reals A, $E_0$, and any real b. Precisely, the above function set constructed via the $k_{max}$ equation system is a representation of the above exponential function family. As a result, the above function set is a superset of the exponential function family required for this problem i.e.:

$$\left\{f: \mathbb{R}_+^* \to \mathbb{R} \;\middle|\; \text{sign}\left(\frac{d^k f(\lambda)}{d\lambda^k}\right) = (-1)^k \forall \lambda \in \mathbb{R}_+^*, k \in [[1, k_{max}]]\right\} \supseteq \quad (9)$$
$$\{f: \mathbb{R}_+^* \to \mathbb{R} \mid f(\lambda) = Ae^{E_0/\lambda} + b, A \in \mathbb{R}_+^*, E_0 \in \mathbb{R}_+^*, b \in \mathbb{R}\}$$

It can be postulated, in one embodiment that, for a sufficiently large $k_{max}$, the above function set (8) is a sufficiently tight superset of the exponential function family.

Using the last result (9) and the finite difference formula, and given a sequence $(\lambda_j)_{j=1\ldots n}$ satisfying $\lambda_{j+1} > \lambda_j \forall j=1 \ldots n-1$, the following equations can be formulated:

$$\text{sign}\left(\frac{df(\lambda)}{d\lambda}\right) = \text{sign}\left(\frac{u_{j+1} - u_j}{\lambda_{j+1} - \lambda_j}\right) = (-1)^1 \forall j=1\ldots n-1 \quad (10)$$

$$\text{sign}\left(\frac{d^2 f(\lambda)}{d\lambda^2}\right) = \quad (11)$$
$$\text{sign}\left(\frac{\frac{u_{j+2} - u_{j+1}}{\lambda_{j+2} - \lambda_{j+1}} - \frac{u_{j+1} - u_j}{\lambda_{j+1} - \lambda_j}}{\lambda_{j+2} - \lambda_j}\right) = (-1)^2 \forall j=1\ldots n-2$$

$$\text{sign}\left(\frac{d^3 f(\lambda)}{d\lambda^3}\right) = \quad (12)$$
$$\text{sign}\left(\frac{\frac{\frac{u_{j+3} - u_{j+2}}{\lambda_{j+3} - \lambda_{j+2}} - \frac{u_{j+2} - u_{j+1}}{\lambda_{j+2} - \lambda_{j+1}}}{\lambda_{j+3} - \lambda_{j+2}} - \frac{\frac{u_{j+2} - u_{j+1}}{\lambda_{j+2} - \lambda_{j+1}} - \frac{u_{j+1} - u_j}{\lambda_{j+1} - \lambda_j}}{\lambda_{j+2} - \lambda_j}}{\lambda_{j+3} - \lambda_j}\right) =$$
$$(-1)^3 \forall j=1\ldots n-3$$

More generally, it can be written:

$$\text{sign}\left(\frac{d^k f(\lambda)}{d\lambda^k}\right) = \text{sign}(D[u_{j_1}, u_{j_2}, \ldots, u_{j_{k+1}} | \lambda_{j_1}, \lambda_{j_2}, \ldots, \lambda_{j_{k+1}}]) = \quad (13)$$
$$(-1)^k \forall j=1\ldots n-k,$$
$$\lambda_{j_1} \leq \lambda_{j_2} \leq \ldots \leq \lambda_{j_{k+1}}$$

Where $D[u_{j_1}, u_{j_2}, \ldots, u_{j_{k+1}} | \lambda_{j_1}, \lambda_{j_2}, \ldots, \lambda_{j_{k+1}}]$ denotes the $k^{th}$ divided difference of the sequence $(u_{j_1}, u_{j_2}, \ldots, u_{j_{k+1}})$ defined recursively as:

$$\begin{cases} D[u_{j_1}, u_{j_2}, \ldots, u_{j_{k+1}} | \lambda_{j_1}, \lambda_{j_2}, \ldots, \lambda_{j_{k+1}}] = \\ \quad \dfrac{D[u_{j_2}, \ldots, u_{j_{k+1}} | \lambda_{j_2}, \ldots, \lambda_{j_{k+1}}] - D[u_{j_1}, \ldots, u_{j_k} | \lambda_{j_1}, \ldots, \lambda_{j_k}]}{\lambda_{j_{k+1}} - \lambda_{j_1}} \\ D[u_{j_2}, u_{j_1} | \lambda_{j_1}, \lambda_{j_2}] = \dfrac{u_{j_2} - u_{j_1}}{\lambda_{j_2} - \lambda_{j_1}} \end{cases} \quad (14)$$

The composition coefficient of the asphaltene constituent, $a_l$, is a function of the u spectrum and can be estimated, in one embodiment, to be within a well-contained linear space in terms of u. That is $l(u) \leq a_l \leq h(u)$, where $l(u)$ and $h(u)$ are hyperplanes in u. Incorporating the Urbach tail and baseline constraints into the set of plausible a solutions culminates in the following set:

$$\{(a_i)_{i=1\ldots l} | \forall i=1\ldots l, \forall j=1\ldots n, \forall k \in [[1, k_{max}]], \\ \forall j_1 < j_2 < \ldots < j_{k+1}, a_i \geq 0, 1-\Delta \leq \Sigma_{i=1}^l a_i \leq 1, \\ a_i^{min} \leq a_i \leq a_i^{max}, 0 \leq m_j - (\Sigma_{i=1}^{l-1} a_i s_{i,j} + u_j + \\ \in_j) \leq \Delta \theta_{max}, -\in_{max} \leq \in_j \leq \in_{max}, \text{sign} \\ (D[u_{j_1}, u_{j_2}, \ldots, u_{j_{k+1}} | \lambda_{j_1}, \lambda_{j_2}, \ldots, \lambda_{j_{k+1}}]) = (-1)^k, l \\ (u) \leq a_l \leq h(u)\} \quad (15)$$

It should be noted that $\text{sign}(D[u_{j_1}, u_{j_2}, \ldots, u_{j_{k+1}} | \lambda_{j_1}, \lambda_{j_2}, \ldots, \lambda_{j_{k+1}}]) = (-1)^k$, $\forall k$ is a linear equation and so is the system characterizing a above.

C. Incorporating Uncertainty Constraints in Basis Spectra Measurements

Generally, the pre-collected basis spectra $\{s_i\}_{i=1\ldots l-1}$ contain inherent errors for a variety of reasons. For example, errors may be introduced because the spectra were collected at inexact temperature and pressure conditions as compared to those of the fluid sample and/or because of the fact that the basis spectra contain inherent errors in spectral measurements. In one embodiment, by assuming that these basis spectra are sampled at sufficiently fine granularity of the temperature and pressure ranges and that the variability of the measurement error within each individual basis spectrum may be contained, such uncertainties may be incorporated into the formulation. The original inequality constraints involving the basis spectra are as follows:

$$0 \leq m_j - (\Sigma_{i=1}^{l-1} a_i s_{i,j} + u_j + \in_j) \leq \Delta \theta_{max} \quad (16)$$

Introducing an error term $e_{i,j}$ for the $i^{th}$ basis spectrum at the $j^{th}$ wavelength channel results in the following:

$$0 \leq m_j - (\Sigma_{i=1}^{l-1} a_i (s_{i,j} + e_{i,j}) + u_j + \in_j) \leq \Delta \theta_{max} \quad (17)$$

By rearranging the terms, we can arrive at the following inequality:

$$\Sigma_{i=1}^{l-1} a_i e_{i,j} m_j - (\Sigma_{i=1}^{l-1} a_i (s_{i,j} + u_j + \in_j) \leq \Delta \theta_{max} + \\ \Sigma_{i=1}^{l-1} a_i e_{i,j} \quad (18)$$

If $e_{i,j}$ admits upper and lower bounds, respectively $e_{i,j}^{max}$ and $e_{i,j}^{min}$, $\forall i=1\ldots l$ and $\forall j=1\ldots n$, then the following is true:

$$\Sigma_{i=1}^{l-1} a_i e_{i,j}^{min} \leq m_j - (\Sigma_{i=1}^{l-1} a_i s_{i,j} + u_j + \in_j) \leq \Delta \theta_{max} + \\ \Sigma_{i=1}^{l-1} a_i e_{i,j}^{max} \quad (19)$$

The final solution set for the composition vector a, which will be referred to herein as P, therefore becomes:

$$P = \{(a_i)_{i=1\ldots l} | \forall i=1\ldots l, \forall j=1\ldots n, \forall k \in [[1, k_{max}]], \forall j_1 < j_2 < \ldots < j_{k+1}, a_i \geq 0, 1-\Delta \leq \Sigma_{i=1}^l a_i \leq 1, \\ a_i^{min} \leq a_i \leq a_i^{max}, \Sigma_{i=1}^{l-1} a_i e_{i,j}^{min} \leq m_j - (\Sigma_{i=1}^{l-1} a_i s_{i,j} + \\ u_j + \in_j) \leq \Delta \theta_{max} + \Sigma_{i=1}^{l-1} a_i e_{i,j}^{max}, -\in_{max} \leq \in_j \leq \in_{max}, \\ \text{sign}(D[u_{j_1}, u_{j_2}, \ldots, u_{j_{k+1}} | \lambda_{j_1}, \lambda_{j_2}, \ldots, \\ \lambda_{j_{k+1}}]) = (-1)^k\} \quad (20)$$

It should be noted that an equivalent solution space characterized in terms of the concentration vector $(c_i)_{i=1\ldots l}$ may be readily obtained by replacing every occurrence of $a_i$ with the ratio $c_i/\rho_i$ $\forall i=1\ldots l$ where $\rho_i$ denotes the density of the $i^{th}$ constituent. Furthermore, any measurement errors in $\rho_i$ can be incorporated in the definition of the set P using similar developments as above.

D. Threshold Corrections Via Optimization

Should the above solution space not yield any solution (i.e., be empty) for a given measured sample fluid spectrum, m, it is likely that one or more of the predefined thresholds are underestimated. The effort of relaxing the thresholds in order to generate a solution set may be cast as an optimization problem. For instance, if it can be suspected that the inherent maximum tool noise $\in_{max}$ needs to be revised, then such a problem may be formulated as below and where $P(\in_{max})$ denotes a parameterization of P in terms of $\in_{max}$.

$$\min_{a, \varepsilon_{max}} \varepsilon_{max} \quad (21)$$

$$\text{Subject to} \begin{cases} \alpha \in P(\varepsilon_{max}) \\ \varepsilon_{max} \geq 0 \end{cases} \quad (22)$$

A similar formulation involving an optimization objective in terms of any combination of thresholds may be made.

E. Approximation of the Original Polytope

Figure 5:
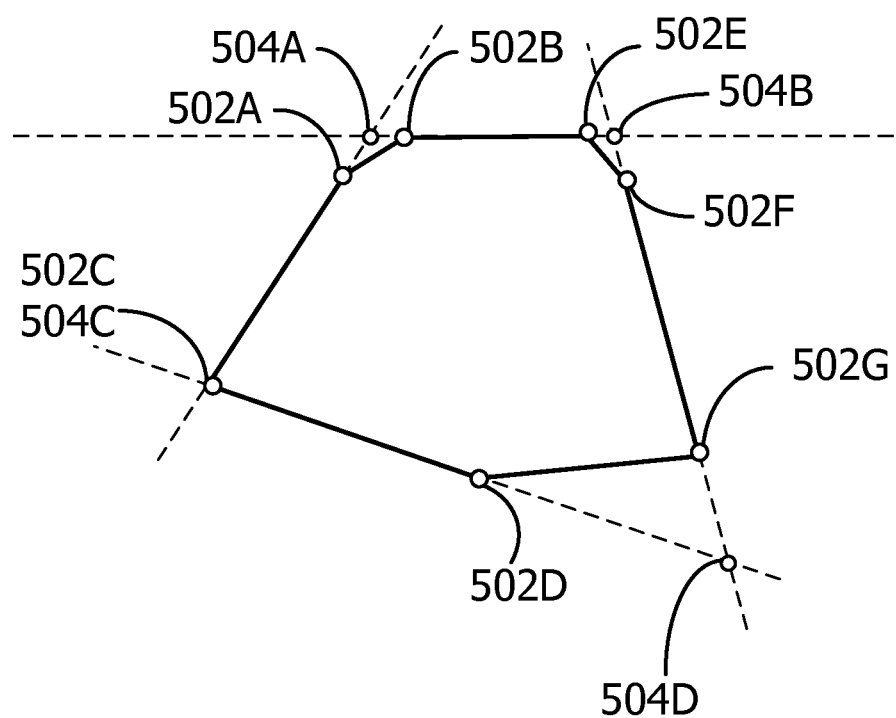
FIG. 5 shows approximation and embedding of the convex hull of FIG. 3, according to one or more disclosed embodiments.

In practice, the polytope defining the solution set, P may have many vertices whose exact enumeration and convex hull simplicial decomposition may become costly computational processes. In the interest of containing the complexity of the process for computing the polytope representation, the original polytope defining the solution set, P is approximated by a sufficiently tight embedding polytope P', in one embodiment. That is $P' \supseteq P$. In practice, this means that the solution space can be approximated by a superset that is more easily manageable. This may be done by computing a set of bounding hyperplanes whose halfspace intersection closely contains that of the original bounding hyperplanes. The computed hyperplanes then define the embedding polytope which defines the solution set P'. A graphical example of polytope approximation via embedding is illustrated in FIG. 5.

As can be seen, the original polytope defined by the seven vertices 502A-502G is approximated by a polytope P' 506 which is defined by only four vertices 504A-504D. Thus, the complexity of the embedding polytope as assessed in terms of the number of bounding hyperplanes and the size of the vertex set is smaller than that of the original polytope.

In one embodiment, the embedding polytope P' is defined via a chosen collection of bounding hyperplanes whose halfspace intersection most tightly encloses the original polytope P. The problem of computing the lower or upper bound of any hyperplane of interest may be set up as a constrained linear optimization problem over P. That is:

$$a_l = \min_{\alpha \in P} a\alpha \quad (23)$$

$$a_u = \max_{\alpha \in P} a\alpha \quad (24)$$

Where the inner product $a\alpha$ represents the equation of a hyperplane of interest without the offset and where $a_l$ and $a_u$ represent the offsets of the tightest lower and upper P-bounding hyperplanes, respectively, amongst all $\{c=a\alpha|c\}$ hyperplanes.

F. Statistical Characterization of P Assuming Uniform Input Probability Distribution Assuming that every point in P is equally probable, then the probability distribution of a over P may be readily obtained from a simplicial decomposition of P. In one embodiment, the distribution over any simplex in the decomposition may be represented via a uniform Dirichlet distribution. The overall distribution may then be the sum of all individual uniform Dirichlet distributions weighted proportionally to the volumes of the respective individual simplices.

Figure 6A:
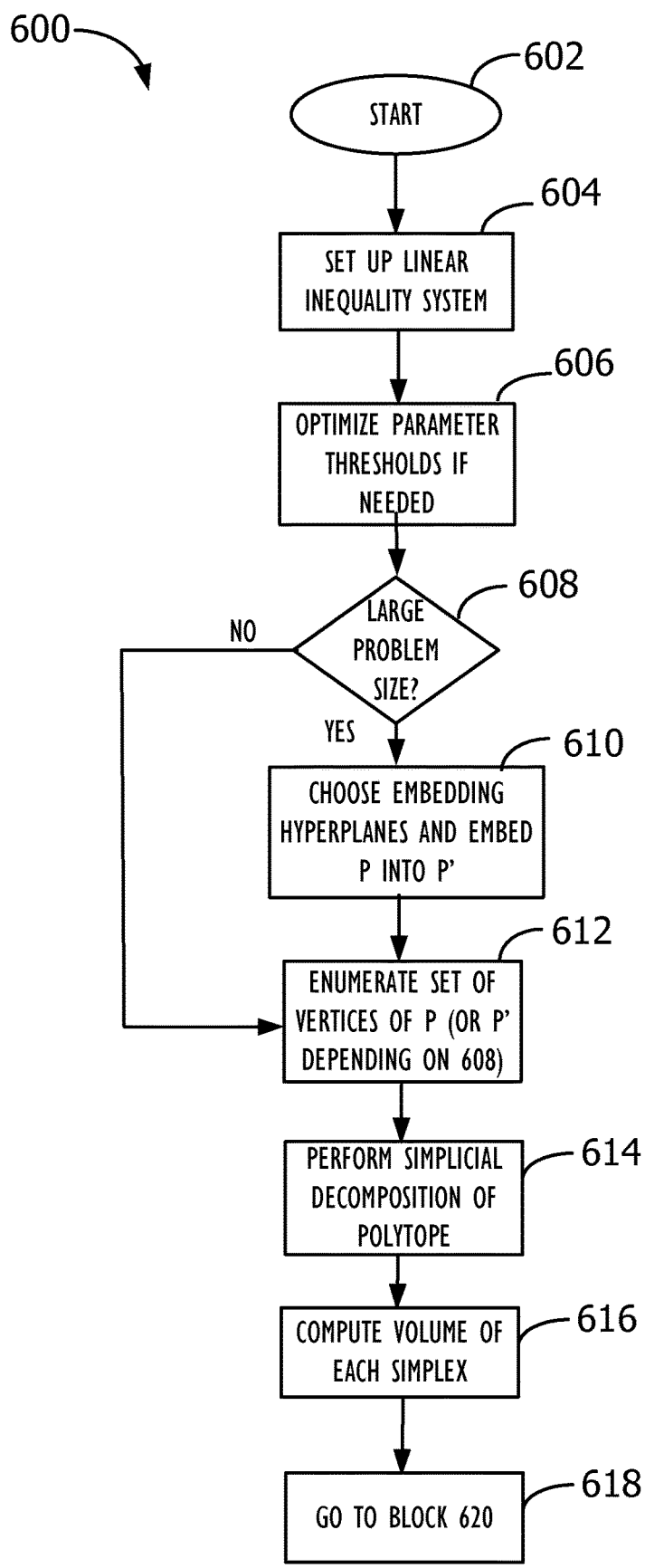
FIG. 6A-6B show a flowchart for computing statistical distribution of fluid composition, according to one or more disclosed embodiments.
Figure 6B:
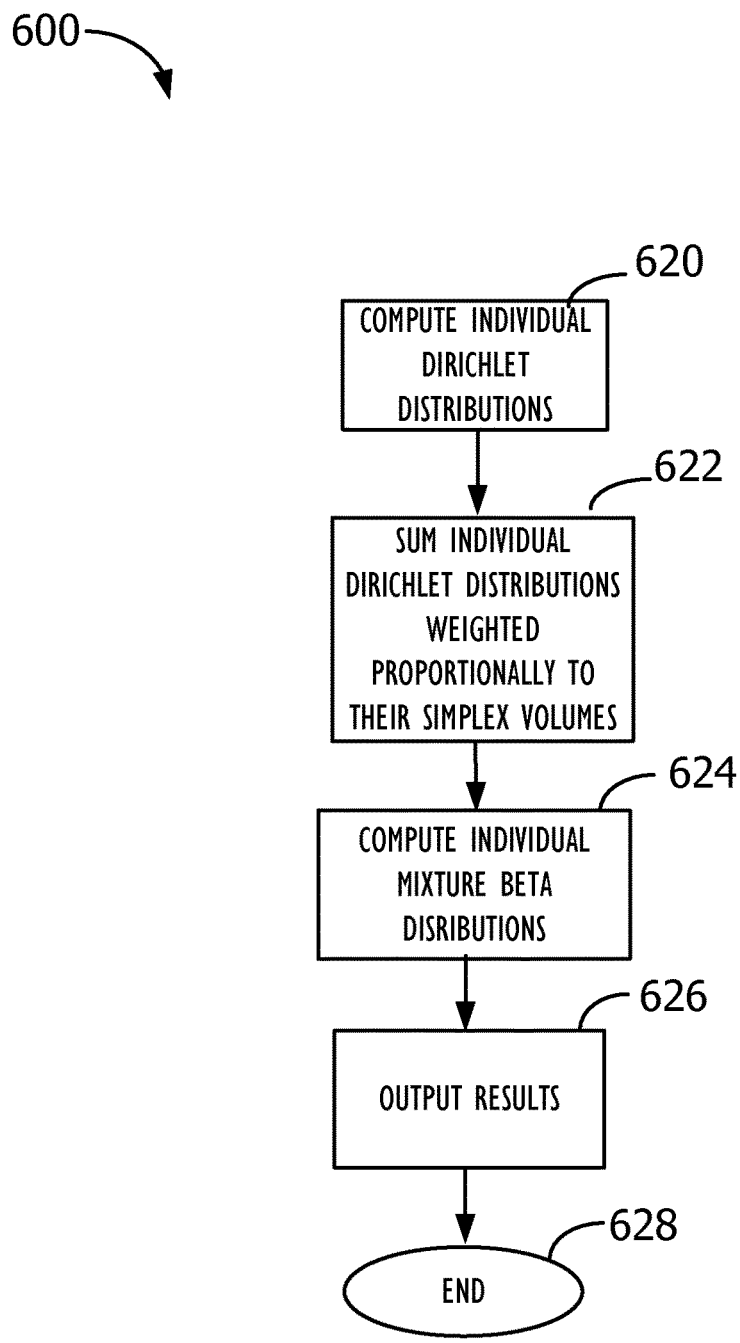

FIGS. 6A-6B provide a flow chart for computing the statistical distribution of the fluid composition mixture coefficients $(a_i)_{i=1\ldots l}$, according to one embodiment. Operation 600 starts (block 602) by setting up a linear inequality system (block 604) which defines the polytope P. In one embodiment, the linear inequality system is defined based on various inputs. The input may include one or more of the following:

$$(m_j)_{j=1\ldots n}, \{S_{i,j}\}_{i=1\ldots l, j=1\ldots n}, (a_i)_{i=1\ldots l}, (a_i^{min})_{i=1\ldots l}, (a_i^{max})_{i=1\ldots l}, (e_{i,j}^{min})_{i=1\ldots l, j=1\ldots n}, (e_{i,j}^{max})_{i=1\ldots l, j=1\ldots n}, k_{max}, \theta_{max}, \in_{max}, \Delta$$

After the linear inequality system yielding the polytope P has been defined, the parameter thresholds are readjusted (i.e. optimized) if needed (block 606) according to the example formulation of (21) and (22). At this stage, it is first determined if the problem size is large (Block 608). That is, a determination is made as to whether or not the problem size defining P which comprises of the 3-tuple $(l, n, k_{max})$ is large. If some chosen largeness criterion evaluated at $(l, n, k_{max})$ is greater than a chosen threshold, characterization of polytope P is determined to be computationally cost-prohibitive to perform. Accordingly, as discussed before, tight bounding hyperplanes are computed to simplify the original polytope P and embed it into a polytope P' (block 610). When the problem size is not determined to be large or after original polytope P has been embedded it into the polytope P', the set of vertices defining the convex hull of the underlying polytope (either P or P' depending on the problem size qualification (Block 608)) are enumerated (block 612).

To simplify characterization of the solution space, the underlying polytope (whether it be P or P'), is decomposed into multiple simplices (block 614). This is done by dissecting the solution space into a set of simplices, given the vertex set defining its convex hull. Once simplicial decomposition has been performed, the volume of each resulting simplex is calculated (block 616), before operation 600 proceeds to block 620 of FIG. 6B.

As discussed before, the solution probability distribution over the entire polytope is the mixture probability distribution obtained from adding up individual Dirichlet distributions over all of the decomposed simplices weighted proportionally to each respective simplex volume. As such, at this stage, all individual Dirichlet distributions are computed (block 620). Once the individual Dirichlet distributions are obtained, they are summed up and weighted proportionally to their simplex volumes (block 622). When the joint probability distribution is a mixture of Dirichlet distributions, then the probability distribution of any individual constituent is a mixture beta distribution. Accordingly, individual mixture beta distributions are calculated (block 624) at this stage. The joint mixture Dirichlet distribution and a desired set of individual mixture beta distributions are then provided as the results (block 626), before operation 600 proceeds to end (block 628).

G. Qualitative Characterization of P Assuming Uniform Input Probability Distribution The statistical distribution of the fluid composition provided by operation 600 of FIGS. 6A-6B gives a complete quantitative set of information about the sample fluid composition. This information may be cast to a qualitative answer which may offer sufficient interpretive value in particular applications which do not require the complete quantitative information. For example, in some applications, whether or not a particular constituent is sufficiently present suffices without having to know the exact levels of its concentration. Such qualitative information may be more accurately predictable than the true quantitative answer. To determine this, in one embodiment, the statistical distribution of constituents of interest which is obtained using operation 600 is indirectly cast to a 3-class state i.e., present, not present, or indeterminate.

This may be done, in one embodiment, by setting a cutoff threshold for each constituent of interest that determines whether or not the underlying constituent is considered sufficiently present. Thus, for a given constituent i and cutoff threshold $\tau$, if $a_i \geq \tau$, then the $i^{th}$ constituent is considered to be present. Otherwise it is absent. Because, in reality, whether or not $a_i \geq \tau$ is generally only inferred probabilistically, we can only assess $p(a_i \geq \tau)$ where $p(.)$ represents some probability function. To be able to interpret $p(a_i \geq \tau)$ as one of the three allowed state classes, a confidence threshold, minConf, is used, in one embodiment. The appropriate state class can then be determined using the following probability based rules:

if $p(a_i \geq \tau) \geq$ minConf then constituent i is present;
if $p(a_i \geq \tau) \geq 1-$minConf then constituent i is not present;
otherwise presence of constituent i is indeterminate.

Figure 7:
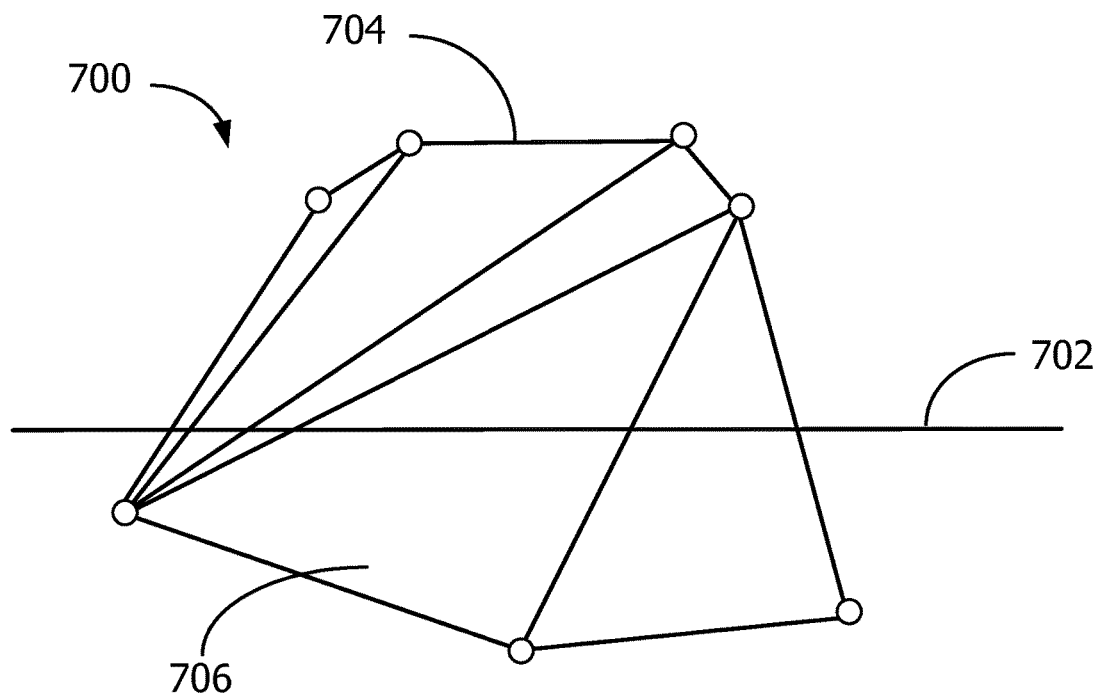
FIG. 7 shows multiple frusta associated with a given simplicial decomposition, according to one or more disclosed embodiments.

Thus, to determine the appropriate class for any given constituent i, the function $p(a_i \geq \tau)$ for that constituent needs to be evaluated. To do so, the hyperplane $a_i = \tau$ is used. In general, the hyperplane $a_i = \tau$ cuts the original polytope P into two portions: an upper portion (the subset of P in the halfspace above the cutting hyperplane) and a lower portion (the subset of P in the halfspace below the cutting hyperplane). This is illustrated in FIG. 7. As shown, the cutting hyperplane 702 divides polytope P into two portions 704 (upper) and 706 (lower). Moreover, one or more of the underlying simplicies in the decomposition may in turn be cut into two portions.

Figure 8:
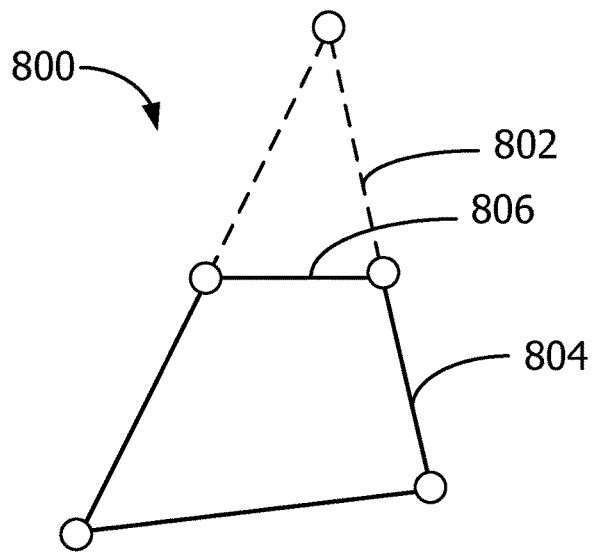
FIG. 8 shows an example frustum, according to one or more disclosed embodiments.

A simplex 800 cut into two parts 802 and 804 as a result of a cutting hyperplane is shown in FIG. 8. Simplex 800 is divided into an upper portion 802 and a lower portion 804 by the hyperplane passing through the segment 806. Assuming uniform probability distribution over P, the function value $p(a_i \geq \tau)$ is then the total space volume within the polytope P that is above $a_i = \tau$ divided by the total volume of P. For the simplex 800, this is the total space volume in the upper portion 802 divided by the total volume of simplex 800. A simplex such as simplex 800 whose top portion (i.e. upper portion 802) is removed by a cutting hyperplane is geometrically referred to as a frustum.

As is shown in FIG. 7, the cut through each simplex generates either a frustum or a set that is the complement of a frustum within the underlying simplex. Hence, computing the volume of the frustum and that of the full simplex suffices for calculating the volume within any simplex that is above a given cut. Procedures for computing the volume of a frustum knowing the original simplex and the given cut are known in the art and are thus not discussed herein. To complete the evaluation of $p(a_i \geq \tau)$, assuming uniform prior probability, it therefore suffices to add up the volumes of all simplicial portions above the given cut and divide that by the total simplex volumes.

Figure 9A:
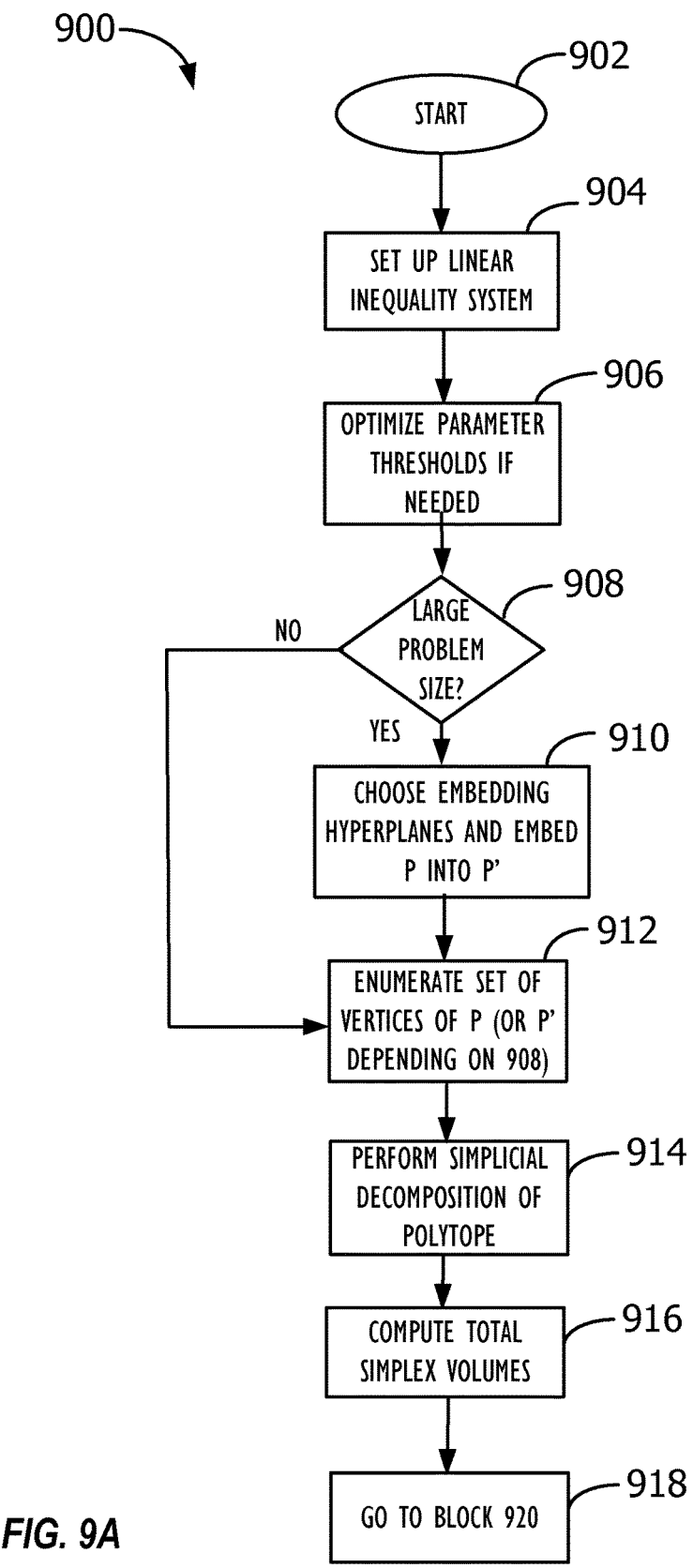
FIGS. 9A-9B show a flowchart for computing qualitative fluid composition information, according to one or more disclosed embodiments.
Figure 9B:
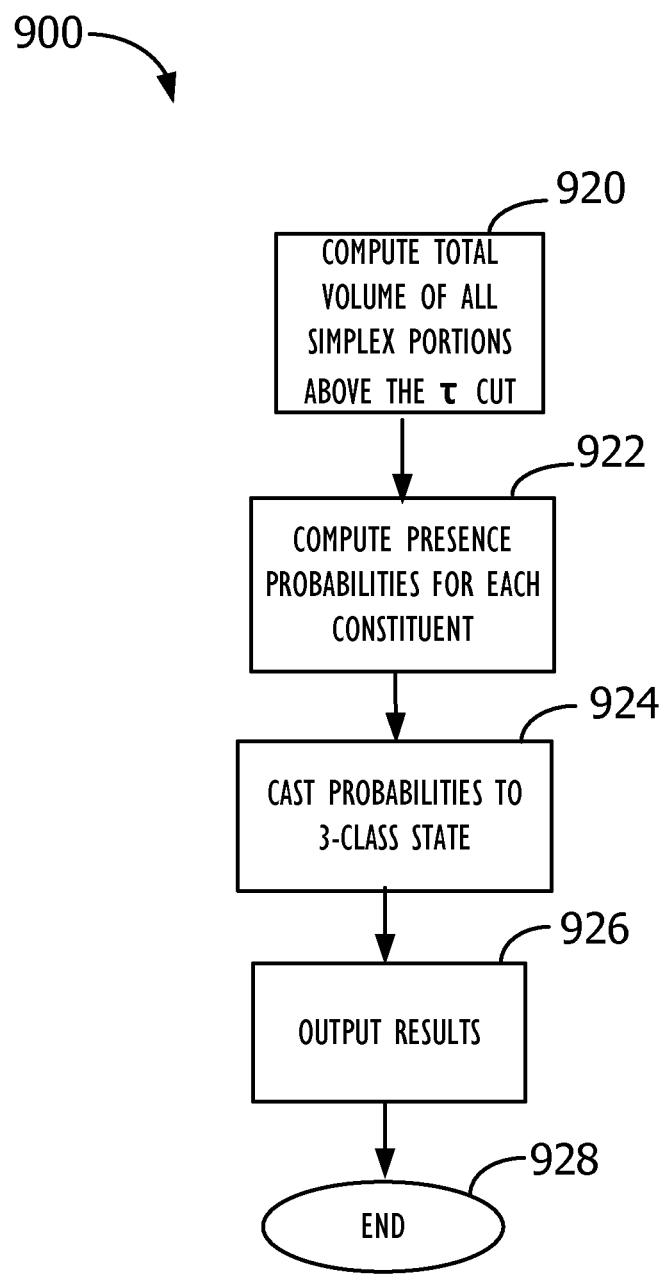

FIGS. 9A-9B provides a flow chart for predicting the qualitative fluid composition information i.e., 3-class states (present, absent, or indeterminate) of all constituents, according to one embodiment. Operation 900 starts (block 902), in a similar manner as operation 600, by setting up a linear inequality system (block 904) which defines the polytope P. In one embodiment, the linear inequality system is defined based on various inputs. The input may include one or more of the following:

$(m_j)_{j=1\ldots m}, \{S_{i,j}\}_{i=1\ldots l, j=1\ldots n}, (a_i)_{i=1\ldots l}, (a_i^{min})_{i=1\ldots l}, (a_i^{max})_{i=1\ldots l}, (e_{i,j}^{min})_{i=1\ldots l, j=1\ldots n}, (e_{i,j}^{max})_{i=1\ldots l, j=1\ldots n}, k_{max}, \theta_{max}, \epsilon_{max}, \Delta$ After the linear inequality system yielding the polytope P has been defined, the parameter thresholds are readjusted (i.e. optimized) if needed (block 906). At this stage, it is first determined if the problem size is large. In one embodiment, this involves determining whether or not the problem size defining P which comprises of the 3-tuple (l, n, $k_{max}$) is large. If some chosen largeness criterion evaluated at (l, n, $k_{max}$) is greater than a chosen threshold, characterization of polytope P is determined to be computationally cost-prohibitive to perform. Accordingly, as discussed before, tight bounding hyperplanes are selected to closely enclose the original polytope P and embed it into a polytope P' (block 910). When the problem size is not large or after the original polytope P has been embedded it into the polytope P', the set of vertices defining the convex hull of the polytope P (or P' depending on determination in block 908) are enumerated (block 912).

To simplify characterization of the solution space, the underlying polytope (whether it be P or P'), is decomposed into multiple simplices (block 914) given the vertex set defining its convex hull. Once simplicial decomposition has been performed, the total volume of the simplices is calculated (block 916). This may be done by calculating the volume of each simplex and adding all of the volumes together to get the total. Operation 900 then proceeds to block 920 of FIG. 9B (block 918).

In order to evaluate $p(a_i \geq \tau)$, the total volume of all simplex portions above the $\tau$ cut is calculated (block 920). This is done, in one embodiment, by calculating the volume of each simplex portion separately and then adding all of the volumes together to get the total. After the said total is calculated, the presence probability for each constituent is calculated (block 922) by dividing the said total by the total of all simplex volumes (total volume of underlying polytope). The presence probability is then cast to the 3-class state (block 924) based on the following rules:

if $p(a_i \geq \tau) \geq$ minConf then constituent i is present;

if $p(a_i \geq \tau) \geq 1-$minConf then constituent i is not present;

otherwise presence of constituent i is indeterminate.

The results are then outputted (block 926) before operation 900 proceeds to end (block 928).

H. Statistical Characterization of P Assuming Arbitrary Input Probability Distribution Operation 600 of FIGS. 6A-6B assumes that all points within the solution space P are all equally probable (i.e., uniform prior). In one embodiment, this assumption is relaxed and the algorithm is generalized to a known arbitrary input probability distribution. One such approach involves assigning each vertex in the computed vertex set V, a weight coefficient that may be deduced from the input prior probability distribution and P. The set of weights of the vertices defining any particular simplex therefore serves to define the particular individual Dirichlet distribution over the same simplex. This is illustrated in the flowchart shown in FIGS. 10A-10B which provide a generalized procedure for computing a statistical distribution of fluid composition, according to one embodiment.

Figure 10A:
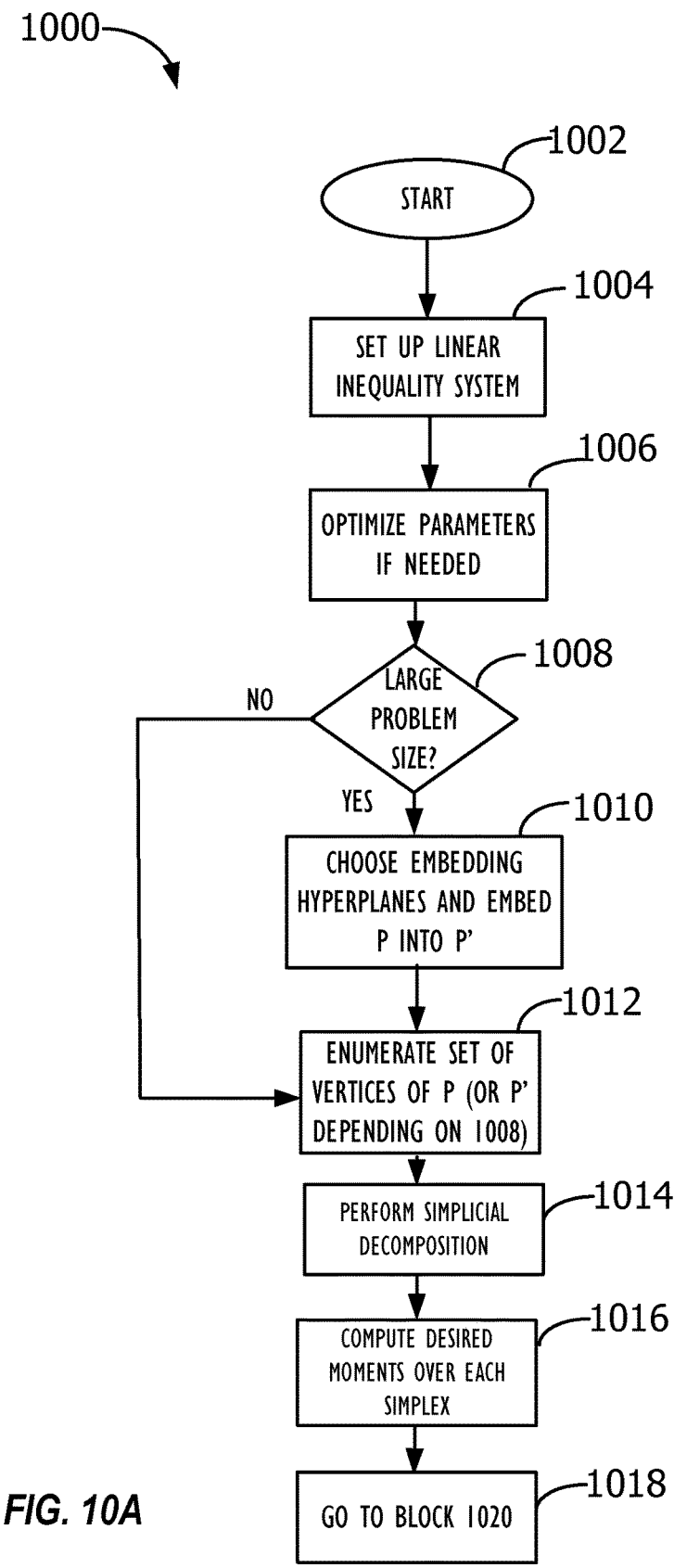
FIG. 10A-10B show a flowchart for computing statistical distribution of fluid composition, according to another one or more disclosed embodiments.
Figure 10B:
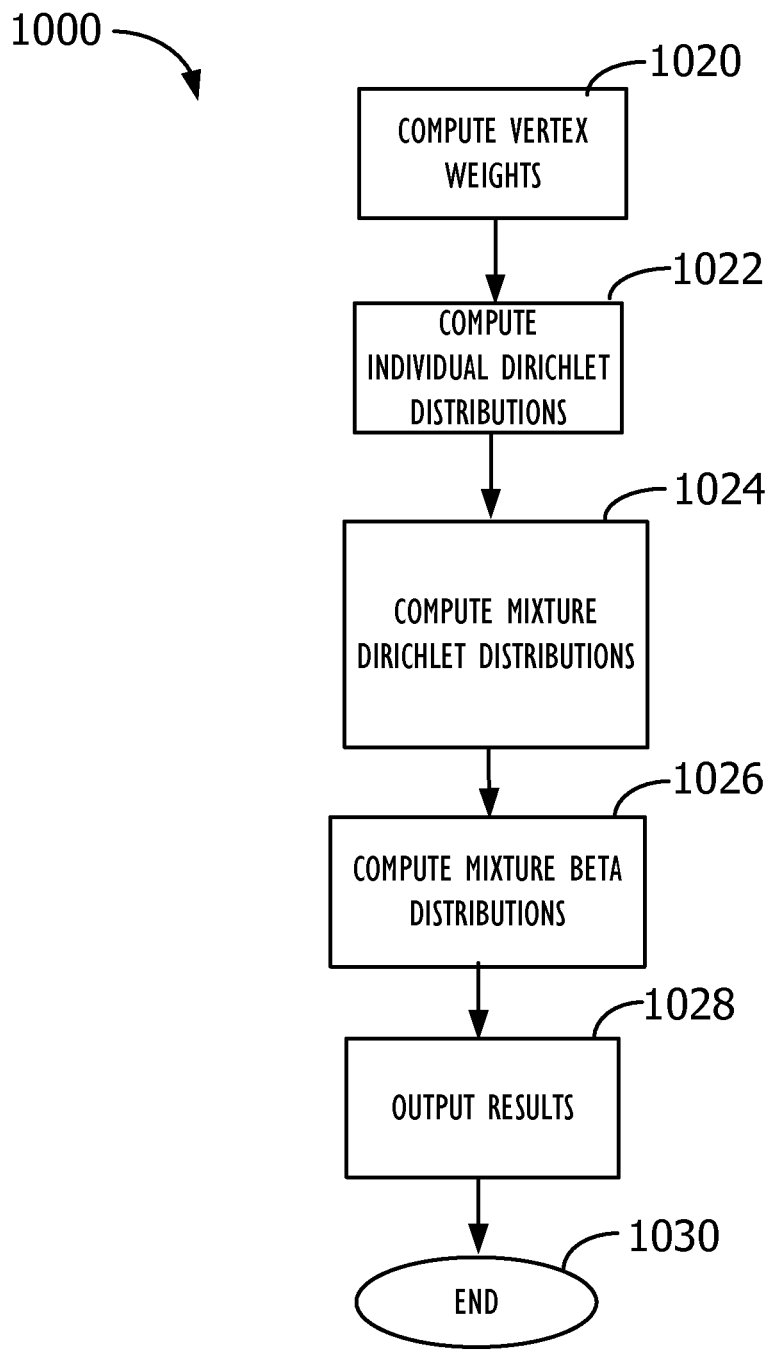

Operation 1000 of FIGS. 10A-10B starts (block 1002), in a similar manner as operation 600, by setting up a linear inequality system (block 1004) which defines the polytope P. In one embodiment, the linear inequality system is defined based on various inputs. The input may include one or more of the following:

$(m_j)_{j=1\ldots n}, \{s_{i,j}\}_{i=1\ldots l, j=1\ldots n}, (\rho_i)_{i=1\ldots l}, (c_i^{min})_{i=1\ldots l},$ $(c_i^{max})_{i=1\ldots l}, (e_{i,j}^{min})_{i=1\ldots l, j=1\ldots n}, (e_{i,j}^{max})_{i=1\ldots l, j=1\ldots n}$ $k_{max}, \theta_{max}, \epsilon_{max}, \Delta$ After the linear inequality system of the polytope P has been defined, the parameter thresholds are readjusted (i.e. optimized) if needed (block 1006). At this stage, it is determined if the problem size is large. In one embodiment, this involves determining whether or not the problem size defining P which comprises of the 3-tuple (l, n, $k_{max}$) is large. If some chosen largeness criterion evaluated at (l, n, $k_{max}$) is greater than a chosen threshold, characterization of polytope P is determined to be computationally cost-prohibitive to perform. Accordingly, as discussed before, a manageable number of tight bounding hyperplanes are computed to closely enclose the original polytope P and embed it into a polytope P' (block 1010). When the problem size is not determined to be large or after original polytope P has been embedded into the polytope P', the set of vertices V defining the convex hull of the polytope P (or P' depending on determination in block 1008) are enumerated (block 1012).

To simplify characterization of the solution space, the underlying polytope (whether it be P or P') is then decomposed into multiple simplices (block 1014) given the vertex set V defining its convex hull.

Operation 1000 then proceeds to block 1016 to compute chosen distribution moments over each simplex in the simplicial decomposition obtained from block 1014, which is essential to computing the vertex set weights and ultimately the overall distribution over P.

To compute distribution moments over any simplex in the decomposition of P, we assume a given prior density function $f(a)$ for all compositions a. Let $\Sigma_P$ denote the simplex collection obtained by the simplicial decomposition of P. The weighted volume of the $k^{th}$ simplex in $\Sigma_P$ is defined as $N_k = \int f(a) da$ (25). The first moment of constituent i over the $k^{th}$ simplex in $\Sigma_P$ may then be written as $$M_{i,k}^1 = \frac{1}{N_k} \int_{\sigma_k} f(\alpha) \alpha_i d\alpha$$

where $\sigma_k$ denotes the $k^{th}$ simplex in the simplex collection $\Sigma_P$. More generally, the $j^{th}$ moment of constituent i over $\sigma_k$ may be written as $$M_{i,k}^j = \frac{1}{N_k} \int_{\sigma_k} f(\alpha) \alpha_i^j d\alpha \quad (26)$$

where $a_i^j$ denotes $a_i$ raised to the power of j.

Operation 1000 then proceeds to block 1020 of FIG. 10B (block 1018), where the weights of all vertices in V are calculated (block 1020). Computing the said weights is based on the set of computed moments according to (26) for all i, j, and k. The weights of the set of vertices of any particular simplex to be calculated are no other than the set of parameters defining the Dirichlet distribution over the same particular simplex and admitting the corresponding moments computed in block 1016.

Denote the set of all the weights from all vertices by $w=\{w_i\}_{i=1 \ldots |V|}$ and by $w^{(k)} \subset w$ the subset of weights corresponding to the $k^{th}$ simplex's vertices. $w^{(k)}$ can be mapped to $\mathcal{M}_{i,k}{}^j$ using formulae known in the art. Abstractly, let $\psi_i{}^j(w^{(k)}) = \mathcal{M}_{i,k}{}^j$ denote the said mapping for the $j^{th}$ moment of constituent i over the $k^{th}$ simplex. The complete set of equations mapping the weights to the moments may be then be expressed as, $$\{\psi_i^j(w^{(k)}) = \mathcal{M}_{i,k}^j\}_{i,j,k} \quad (27)$$

The set of equations (27) may not yield a solution w* if the given moments cannot be cast to a Dirichlet distribution for one or more simplices. To this end, let $d_j(\psi_i{}^j(w^{(k)}), \mathcal{M}_{i,k}{}^j)$ be a distance metric between the mapped moment $\psi_i{}^j(w^{(k)})$ and the calculated homologue $\mathcal{M}_{i,k}{}^j$. An optimal w* can therefore be obtained from the following optimization problem to yield the desired set of vertex weights, $$w^* = \underset{w}{\mathrm{argmin}} \sum_{i,j,k} d_j(\psi_i^j(w^{(k)}), \mathcal{M}_{i,k}^j) \quad (28)$$

After weights of all vertices in V are calculated, individual Dirichlet distributions over each simplex in the decomposition are computed with parameters corresponding to the associated simplex's vertex weights (block 1022). Once the individual Dirichlet distributions are obtained, all of them are summed, weighted proportionally to their respective weighted simplex volumes relative to the total weighted volume (block 1024) from all simplices. Mixture beta distributions are next calculated (block 1026) for each of a desired set of constituents (block 1026). The joint mixture Dirichlet distribution and a desired set of mixture beta distributions are then provided as the results (block 1028), before operation 1000 proceeds to end (block 1030).

I. Qualitative Characterization of P Assuming Arbitrary Input Probability Distribution Computing qualitative fluid mixture flags assuming non-uniform prior distribution $f(a)$ can be done by exploiting the output of operation 1000 of FIGS. 10A-10B. For any constituent i, its mixture beta distribution can be integrated over the range [Δ,1] to yield $p(a_i \geq \tau)$. To cast $p(a_i \geq \tau)$ to the 3-class state flag, the same rules as before may be used:

if $p(a_i \geq \tau) \geq \mathrm{minConf}$ then constituent i is present;
if $p(a_i \geq \tau) \geq 1 - \mathrm{minConf}$ then constituent i is not present;
otherwise presence of constituent i is indeterminate.

J. System

Figure 11:
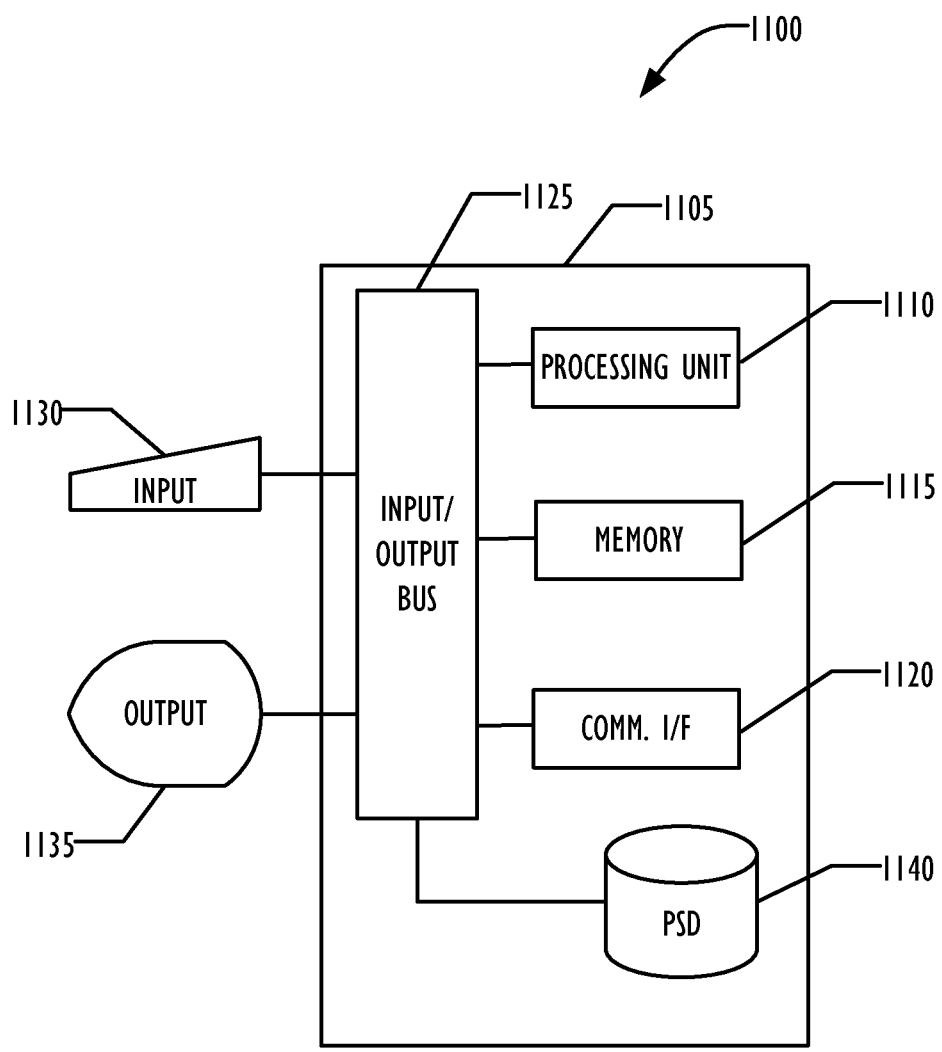
FIG. 11 is a block diagram illustrating a device which could be used as part of a system to execute the fluid composition approaches described herein according to one or more disclosed embodiments.

Referring now to FIG. 11, an example processing device 1100 for use in performing the fluid composition characterization techniques discussed herein according to one embodiment is illustrated in block diagram form. Processing device 1100 may serve as processor in a tool, a server, a computer, or the like. Example processing device 1100 includes a system unit 1105 which may be optionally connected to an input device 1130 and output device 1135. A program storage device (PSD) 1140 (sometimes referred to as a hard disk, flash memory, or non-transitory computer readable medium) is included with the system unit 1105. Also included with system unit 1105 is a communication interface 420 for communication via a network with other remote and/or embedded devices (not shown). Communication interface 1120 may be included within system unit 1105 or be external to system unit 1105. In either case, system unit 1105 will be communicatively coupled to communication interface 1120. Program storage device 1140 represents any form of non-volatile storage including, but not limited to, all forms of optical and magnetic memory, including solid-state, storage elements, including removable media, and may be included within system unit 1105 or be external to system unit 1105. Program storage device 1140 may be used for storage of software to control system unit 1105, data for use by the processing device 1100, or both.

System unit 1105 may be programmed to perform methods in accordance with this disclosure. System unit 1105 also includes one or more processing units 1110, input-output (I/O) bus 1125 and memory 1115. Access to memory 1115 can be accomplished using the input-output (I/O) bus 1125. Input-output (I/O) bus 1125 may be any type of interconnect including point-to-point links and busses. Processing unit 1110 may include any programmable controller device including, for example, a suitable processor. Memory 1115 may include one or more memory modules and comprise random access memory (RAM), read only memory (ROM), programmable read only memory (PROM), programmable read-write memory, and solid-state memory. As noted above, embodiments of the inventions disclosed herein may include software. As such, we shall provide a description of common computing software architecture. Like the hardware examples, the software architecture discussed here is not intended to be exclusive in any way but rather illustrative.

Figure 12:
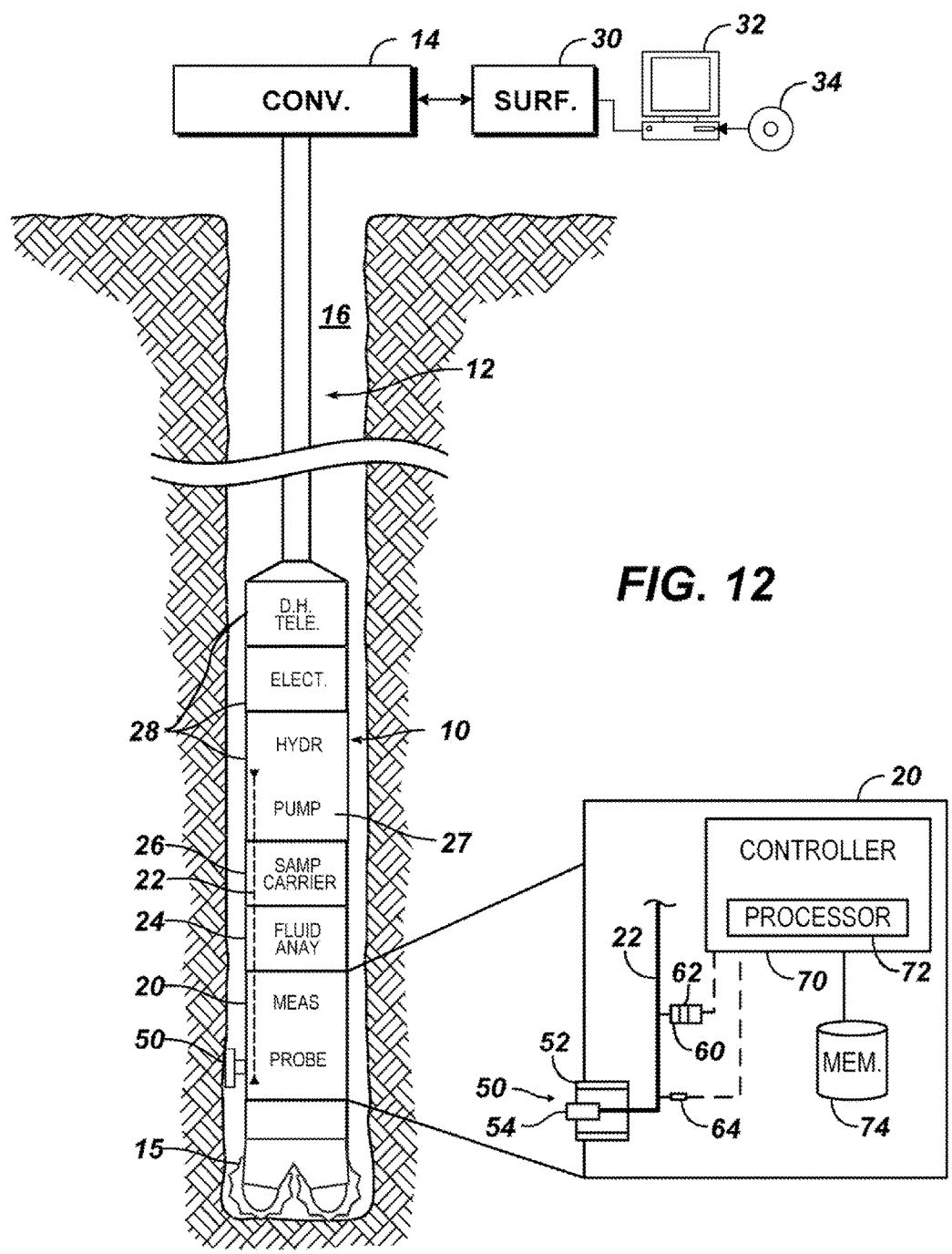
FIG. 12 illustrates one application for performing fluid composition characterization techniques according to the present disclosure to analyze the composition of formation fluid obtained with a formation-testing tool in a borehole.

FIG. 12 shows one application for performing fluid composition characterization techniques according to the present disclosure to analyze the composition of formation fluid in a borehole. In this application of FIG. 12, a downhole tool 10 analyzes fluid measurements from a formation. A conveyance apparatus 14 at the surface deploys the downhole tool 10 in a borehole 16 using a drill string, a tubular, a cable, a wireline, or other component 12.

The tool 10 can be any tool used for wireline formation testing, production logging, Logging While Drilling/Measurement While Drilling (LWD/MWD), or other operations. For example, the tool 10 as shown in FIG. 12 can be part of an early evaluation system disposed on a drill collar of a bottomhole assembly having a drill bit 15 and other necessary components. In this way, the tool 10 can analyze the formation fluids shortly after the borehole 16 has been drilled. As such, the tool 10 can be a Fluid-Sampling-While-Drilling (FSWD) tool. Alternatively, the tool 10 can be a wireline pump-out formation testing (WPFT) tool or any other type of testing tool.

In use, the tool 10 obtains formation fluids and measurements at various depths in the borehole 16 to determine properties of the formation fluids in various zones. To do this, the tool 10 can have a probe 50, a measurement device 20, and other components for in-situ sampling and analysis of formation fluids in the borehole 16. Rather than a probe 50, the tool 10 can have an inlet with straddle packers or some other known sampling component.

In general, any suitable type of formation testing inlet known in the art can be used, with some being more beneficial than others. Also, the disclosed analysis can be used with any type of drilling mud, such as oil-based or water-based muds.

During the sampling process, measurements are recorded in a memory unit 74, communicated or telemetered uphole for processing by surface equipment 30, or processed locally by a downhole controller 70. Each of these scenarios is applicable to the disclosed fluid composition analysis.

Although only schematically represented, it will be appreciated that the controller 70 can employ any suitable processor 72, program instructions, memory 74, and the like for achieving the purposes disclosed herein. The surface equipment 30 can be similarly configured. As such, the surface equipment 30 can include a general-purpose computer 32 and software 34 for achieving the purposes disclosed herein.

The tool 10 has a flow line 22 that extends from the probe 50 (or equivalent inlet) and the measurement section 20 through other sections of the tool 10. The inlet obtains fluid from the formation via the probe 50, isolation packers, or the like. As noted above, any suitable form of probe 50 or isolation mechanism can be used for the tool's inlet. For example, the probe 50 can have an isolation element 52 and a snorkel 54 that extend from the tool 10 and engage the borehole wall. A pump 27 lowers pressure at the snorkel 54 below the pressure of the formation fluids so the formation fluids can be drawn through the probe 50.

In a particular measurement procedure of the probe 50, the tool 10 positions at a desired location in the borehole 16, and an equalization valve (not shown) of the tool 10 opens to equalize pressure in the tool's flow line 22 with the hydrostatic pressure of the fluid in the borehole 16. A pressure sensor 64 measures the hydrostatic pressure of the fluid in the borehole. Commencing operations, the probe 50 positions against the sidewall of the borehole 16 to establish fluid communication with the formation, and the equalization valve closes to isolate the tool 10 from the borehole fluids. The probe 50 then seals with the formation to establish fluid communication.

At this point, the tool 10 draws formation fluid into the tool 10 using a fluid pumping module and the like. Sensors in the tool 10 measure the density and other physical properties of the fluid, and optical sensors in the tool 10 measure the absorption spectrum of the sample fluid at various wavelength channels. At various points, components such as valves, channels, chambers, and the pump 27 on the tool 10 operate to draw fluid from the formation that can be analyzed in the tool 10 and/or stored in one or more sample chambers 26. Eventually, the probe 50 can be disengaged, and the tool 10 can be positioned at a different depth to repeat the cycle.

Because the intention is to determine properties and constituents of the formation fluid, obtaining uncontaminated sampled fluid with the probe 50 is important. The sampled fluid can be contaminated by drilling mud because the probe 50 has made a poor seal with borehole wall because mud filtrate has invaded the formation, and/or dynamic filtration through the mudcake establishes an equilibrium inflow during pump-out operations. Therefore, the fluid can contain hydrocarbon components (solids, liquids, and/or supercritical gas) as well as drilling mud filtrate (e.g., water-based mud or oil-based mud) or other contaminants. The drawn fluid flows through the tool's flow line 22, and various instruments and sensors (20 and 24) in the tool 10 analyze the fluid.

For example, the probe 50 and measurement section 20 can have sensors that measure various physical parameters (i.e., pressure, flow rate, temperature, density, viscosity, resistivity, capacitance, etc.) of the obtained fluid, and a measurement device, such as a spectrometer or the like, in a fluid analysis section 24 can determine physical and chemical properties of oil, water, and gas constituents of the fluid downhole using optical sensors. Eventually, fluid directed via the flow line 22 can either be purged to the annulus or can be directed to the sample carrier section 26 where the samples can be retained for additional analysis at the surface.

Additional components 28 of the tool 10 can hydraulically operate valves, move formation fluids and other elements within the tool 10, can provide control and power to various electronics, and can communicate data via wireline, fluid telemetry, or other method to the surface. Uphole, surface equipment 30 can have a surface telemetry unit (not shown) to communicate with the downhole tool's telemetry components. The surface equipment 30 can also have a surface processor (not shown) that performs processing of the data measured by the tool 10 in accordance with the present disclosure.

In the description, for purposes of explanation, numerous specific details are set forth in order to provide a thorough understanding of the inventive concept. As part of this description, some of this disclosure's drawings represent structures and devices in block diagram form in order to avoid obscuring the invention. Reference in this disclosure to "one embodiment" or to "an embodiment" means that a particular feature, structure, or characteristic described in connection with the embodiment is included in at least one embodiment of the invention, and multiple references to "one embodiment" or "an embodiment" should not be understood as necessarily all referring to the same embodiment.

It will be appreciated that in the development of any actual implementation (as in any development project), numerous decisions must be made to achieve the developers' specific goals (e.g., compliance with system- and business-related constraints), and that these goals will vary from one implementation to another. It will also be appreciated that such development efforts might be complex and time-consuming, but would nevertheless be a routine undertaking for those of ordinary skill in the art of data processing having the benefit of this disclosure.

In the foregoing description, for purposes of explanation, specific details are set forth in order to provide a thorough understanding of the disclosed embodiments. It will be apparent, however, to one skilled in the art that the disclosed embodiments may be practiced without these specific details. In other instances, structure and devices are shown in block diagram form in order to avoid obscuring the disclosed embodiments. References to numbers without subscripts or suffixes are understood to reference all instance of subscripts and suffixes corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one disclosed embodiment, and multiple references to "one embodiment" or "an embodiment" should not be understood as necessarily all referring to the same embodiment.

It is also to be understood that the above description is intended to be illustrative, and not restrictive. For example, above-described embodiments may be used in combination with each other and illustrative process acts may be performed in an order different than discussed. Many other embodiments will be apparent to those of skill in the art upon reviewing the above description. The scope of the invention therefore should be determined with reference to the appended claims, along with the full scope of equivalents to which such claims are entitled. In the appended claims, terms "including" and "in which" are used as plain-English equivalents of the respective terms "comprising" and "wherein."

What is claimed is:

1. A method of characterizing composition of a fluid, the method comprising:
    obtaining a sample of fluid from a source location in a downhole formation using a probe of a downhole tool disposed in a borehole through the downhole formation;
    obtaining, using an optical sensor of the downhole tool, an absorption spectrum of the sample fluid over a set of one or more wavelength channels;
    receiving, from memory at at least one processing device, a set of basis spectra for one or more constituents of the sample fluid;
    calculating, using the at least one processing device, one or more constraints based on the absorption spectrum and one or more properties of the one or more constituents; and
    characterizing, using the at least one processing device, a solution space for the composition of the sample fluid in terms of the one or more constituents based on the absorption spectrum, the basis spectra, and the one or more constraints by calculating a linear inequality system defining at least one polyhedral solution set and calculating distribution for the one or more constituents over each of one or more simplices created by a simplicial decomposition performed on a vertex set enumerated from the at least one polyhedral solution set; and
    associating, using the at least one processing device, the solution space for the composition with the source location of the sample fluid.

2. The method of claim 1, wherein obtaining the absorption spectrum of the sample fluid over the set of one or more wavelength channels comprises generating the absorption spectrum of the sample fluid at the set of the wavelength channels by utilizing the optical sensor of the downhole tool.

3. The method of claim 1, wherein receiving the set of the basis spectra for the one or more constituents of the sample fluid comprises obtaining the set of the basis spectra from a stored collection of base constituent spectra at a plurality of temperatures and pressures.

4. The method of claim 1, wherein at least one of the one or more constraints comprises one or more of:
    a maximum tool measurement error on any one of the one or more wavelength channels;
    a maximum measurable absorption value on any one of the one or more wavelength channels;
    maximum and minimum mixture coefficient thresholds for at least one of the one or more constituents;
    a set of linear constraints that can be used to approximate a general form of a cumulative spectrum of an Urbach tail and baseline offset;
    a required sum of the mixture coefficients of the one or more constituents;
    a required mixture of the basis spectra, the Urbach tail, and the baseline offset relative to obtained spectrum of a fluid sample; and
    upper and lower bounds on a level of error in obtained absorption in each spectrum in the set of basis spectra over each of the one or more wavelength channels.

5. The method of claim 1, further comprising obtaining a density value for each one of the one or more constituents and the sample fluid.

6. The method of claim 1, further comprising obtaining a joint prior density function for the mixture coefficients of the one or more constituents.

7. The method of claim 1, wherein characterizing the solution space for the composition of the sample fluid comprises:
    calculating the linear inequality system defining a complete polyhedral solution set for the at least one polyhedral solution set;
    adjusting one or more parameter thresholds to ensure a non-empty solution set for the complete polyhedral solution set;
    approximating the complete polyhedral solution set by embedding the complete polyhedral solution set into a polyhedral solution set of lesser complexity;
    enumerating the vertex set of the complete or embedded polyhedral solution set;
    performing the simplicial decomposition on the enumerated vertex set to create the one or more simplices;
    calculating a volume of each of the one or more simplices;
    calculating the distribution as a Dirichlet distribution over each of the one or more simplices; and
    calculating the distribution as a beta distribution over each of the one or more simplices for each of the one or more constituents from the Dirichlet distribution.

8. The method of claim 7, wherein calculating the volume of each of the one or more simplices comprises integrating the joint prior density function over each of the one or more simplices.

9. The method of claim 7, wherein characterizing the solution space for the composition of the sample fluid comprises calculating a weight value for each enumerated vertex in the enumerated vertex set based on a joint prior density function for the mixture coefficients of the one or more constituents and a performed simplicial decomposition.

10. The method of claim 9, wherein the weight value for each enumerated vertex in the vertex set is calculated based on a set of distribution moments over each of the one or more simplices in the simplicial decomposition.

11. The method of claim 10, wherein the set of distribution moments is calculated by performing integration of appropriate integrands over each of the one or more simplices in the simplicial decomposition and based on the joint prior density function.

12. The method of claim 9, wherein calculating the vertex weight values for each enumerated vertex in the vertex set is obtained as a result of an optimization method for casting the distribution over each of the one or more simplices in the simplicial decomposition from the calculated distribution moments.

13. The method of claim 7, wherein characterizing the solution space for the composition of the sample fluid comprises calculating the volume of each of the one or more simplices based on a joint prior density function.

14. The method of claim 7, wherein characterizing the solution space for the composition of the fluid sample comprises calculating a mixture Dirichlet distribution over the complete polyhedral set.

15. The method of claim 14, wherein the mixture beta distribution is calculated from the mixture Dirichlet distribution over the complete polyhedral set for each of the one or more constituents.

16. The method of claim 14, wherein the mixture Dirichlet distribution is calculated by linearly combining individual Dirichlet distributions.

17. The method of claim 16, wherein linearly combining individual Dirichlet distributions comprises calculating weighting values based on respective simplex volumes relative to a total polyhedral volume.

18. The method of claim 14, further comprising obtaining a minimum confidence threshold and a minimum presence threshold for each of the one or more constituents.

19. The method of claim 14, further comprising calculating, using the mixture Dirichlet distribution, a qualitative state for each of the one or more constituents based on obtained minimum confidence and minimum presence thresholds.

20. The method of claim 1, wherein associating the solution space for the composition with the source location of the sample fluid comprises associating the solution space with a portion of the downhole formation traversed by the borehole.

21. A non-transitory program storage device, readable by a processor and comprising instructions stored thereon to cause one or more processors to perform a method for characterizing composition of a sample fluid according to any one of claims 1 to 20.

22. A system for characterizing composition of fluid, the system comprising:
    a downhole tool having a probe to obtain a sample of fluid from a source location in a formation and having an optical sensor to obtain an absorption spectrum of the sample fluid over a set of one or more wavelength channels;
    a memory;
    a communication interface; and
    at least one processing device operatively coupled to the memory and the communication interface and adapted to execute program code stored in the memory to perform a method for characterizing composition of a sample fluid according to any one of claims 1 to 20.

23. A method of characterizing composition of fluid, the method comprising:
    obtaining a sample of fluid from a source location in a downhole formation using a probe of a downhole tool disposed in a borehole through the downhole formation;
    obtaining, using an optical sensor of the downhole tool, an absorption spectrum of the sample fluid over a set of one or more wavelength channels;
    receiving, from memory at at least one processing device, a set of basis spectra for one or more constituents of the sample fluid;
    calculating, using the at least one processing device, one or more constraints based on the absorption spectrum and one or more properties of the one or more constituents; and
    calculating, using the at least one processing device, one or more qualitative states for the one or more constituents based on the absorption spectrum, basis spectra, and the one or more constraints by calculating a linear inequality system defining at least one polyhedral solution set, calculating a volume for each of one or more simplices created from a simplicial decomposition performed on a vertex set enumerated of the at least one polyhedral solution set; calculating a volume of each of one or more frusta generated from a division of at least one of the one or more simplices by a hyperplane defined by a minimum presence threshold; and calculating state probabilities for each of the one or more constituents based on a minimum confidence threshold, the one or more simplex volumes, and the one or more frustum volumes.

24. The method of claim 23, wherein at least one of the one or more constraints comprises one or more of:
    a maximum tool measurement error on any one of the one or more wavelength channels;
    a maximum measurable absorption value on any one of the one or more wavelength channels;
    maximum and minimum mixture coefficient thresholds for at least one of the one or more constituents;
    a set of linear constraints that can be used to approximate a general form of a cumulative spectrum of an Urbach tail and baseline offset;
    required sum of mixture coefficients of the one or more constituents;
    required mixture of basis spectra, Urbach tail, and baseline offset relative to obtained spectrum of a fluid sample;
    upper and lower bounds on a level of error in obtained absorption in each spectrum in the set of basis spectra over each of the one or more wavelength channels;
    the minimum presence threshold; and
    the minimum confidence threshold.

25. The method of claim 23, further comprising obtaining a density value for each one of the one or more constituents and the fluid sample; and incorporating the density values in the one or more constraints.

26. The method of claim 23, wherein calculating the one or more qualitative states comprises:
    calculating the linear inequality system defining a complete polyhedral solution set for the at least one polyhedral solution set;
    adjusting one or more parameter thresholds to ensure a non-empty solution set for the complete polyhedral solution set;
    approximating the complete polyhedral solution set by embedding the complete polyhedral solution set into a polyhedral solution set of lesser complexity;
    enumerating the vertex set of the complete or embedded polyhedral solution set;
    performing the simplicial decomposition on the enumerated vertex set to create the one or more simplices;
    calculating the volume for each of the one or more simplices;
    dividing the at least one of the one or more simplices into a frustum and a remaining portion by the hyperplane defined by the minimum presence threshold;
    calculating the volume of the each of the generated one or more frusta; and
    calculating the one or more qualitative states for the one or more constituents by calculating the state probabilities for each of the one or more constituents based on the minimum confidence threshold, the one or more simplex volumes, and the one or more frustum volumes.

* * * * *